US012704516B2

(12) United States Patent
Lu et al.

(10) Patent No.: US 12,704,516 B2
(45) Date of Patent: Aug. 11, 2026

(54) METHODS AND COMPOSITIONS FOR RAPID DIRECT DETECTION AND DIFFERENTIATION OF INFECTIOUS FROM NONINFECTIOUS VIRUS

(71) Applicants: The Board of Trustees of the University of Illinois, Urbana, IL (US); Universidad Nacional de La Plata, La Plata (AR); Consejo Nacional de Investigaciones Cientificas y Tecnicas, Caba (AR)

(72) Inventors: Yi Lu, Champaign, IL (US); Ana Sol Peinetti, Urbana, IL (US); Omar Azzaroni, La Plata (AR)

(73) Assignees: The Board of Trustees of the University of Illinois, Urbana, IL (US); Universidad Nacional de La Plata, La Plata (AR); Consejo Nacional de Investigaciones Cientificas y Tecnicas, Caba (AR)

( * ) Notice: Subject to any disclaimer, the term of this patent is extended or adjusted under 35 U.S.C. 154(b) by 847 days.

(21) Appl. No.: 17/926,474

(22) PCT Filed: May 19, 2021

(86) PCT No.: PCT/US2021/033245

§ 371 (c)(1),
(2) Date: Nov. 18, 2022

(87) PCT Pub. No.: WO2021/236828

PCT Pub. Date: Nov. 25, 2021

(65) Prior Publication Data

US 2023/0184767 A1 Jun. 15, 2023

Related U.S. Application Data

(60) Provisional application No. 63/027,799, filed on May 20, 2020.

(51) Int. Cl.
*C12Q 1/70* (2006.01)
*G01N 27/327* (2006.01)
(Continued)

(52) U.S. Cl.
CPC ... *G01N 33/56983* (2013.01); *G01N 27/3276* (2013.01); *G01N 27/333* (2013.01); *G01N 33/5308* (2013.01); *G01N 33/5438* (2013.01)

(58) Field of Classification Search
None
See application file for complete search history.

(56) References Cited

U.S. PATENT DOCUMENTS 10,246,741 B2 4/2019 Clarke et al.
2017/0089899 A1 3/2017 Kundrod et al.
(Continued)

FOREIGN PATENT DOCUMENTS

AU 2013220156 8/2013
KR 20170012761 2/2017
(Continued)

OTHER PUBLICATIONS

Arima et al., "Identifying Single Viruses Using Biorecognition Solid-State Nanopores," *J. Am. Chem. Soc.*, vol. 140, pp. 16834-16841, 2018.

(Continued)

*Primary Examiner* — M Franco G Salvoza
(74) *Attorney, Agent, or Firm* — Klarquist Sparkman, LLP

(57) ABSTRACT

Methods of detecting presence of a virus in a sample are provided, the method including contacting the sample with a solid state nanopore comprising a plurality of virus-specific aptamers and measuring a current-voltage curve in the solid state nanopore, wherein a decrease in the current indicates presence of the virus in the sample. Solid state
(Continued)

nanopores comprising a plurality of virus-specific aptamers covalently linked to the interior of the solid state nanopore are also provided. Membranes including a plurality of solid state nanopores including a plurality of covalently attached virus-specific aptamers and kits and systems with a membrane including a plurality of solid state nanopores including a plurality of covalently attached virus-specific aptamers are also provided.

21 Claims, 20 Drawing Sheets

Specification includes a Sequence Listing.

(51) Int. Cl.

| | |
|---|---|
| ***G01N 27/333*** | (2006.01) |
| ***G01N 33/53*** | (2006.01) |
| ***G01N 33/543*** | (2006.01) |
| ***G01N 33/569*** | (2006.01) |

(56) References Cited

U.S. PATENT DOCUMENTS

| | | | |
|---|---|---|---|
| 2017/0096670 | A1 | 4/2017 | Gariepy et al. |
| 2017/0114420 | A1 | 4/2017 | Jaykus et al. |
| 2018/0188230 | A1 | 7/2018 | Huff et al. |
| 2019/0241949 | A1 | 8/2019 | Clarke et al. |
| 2019/0346431 | A1 | 11/2019 | Maglia et al. |

FOREIGN PATENT DOCUMENTS

| | | | | |
|---|---|---|---|---|
| WO | WO-2012021149 | A1 * | 2/2012 | C12Q 1/6869 |
| WO | WO-2012142174 | A1 * | 10/2012 | G01N 33/48721 |
| WO | WO-2015192050 | A1 * | 12/2015 | G01N 33/5308 |
| WO | WO-2016166232 | A1 * | 10/2016 | G01N 33/6872 |
| WO | WO-2017098322 | A1 * | 6/2017 | G01N 33/48721 |
| WO | WO-2020126435 | A1 * | 6/2020 | C12N 15/115 |

OTHER PUBLICATIONS

Bruno et al., "Development, Screening, and Analysis of DNA aptamer libraries potentially useful for diagnosis and passive immunity of arboviruses," *BMC Res. Notes* 5:633, 2012 (12 pages).

Dolai et al., "Whole virus detection using aptamers and paper-based sensor potentiometry," *Med. Devices Sens.* 3:e10112, 2020 (9 pages).

GenBank Accession No. JI784651.1, Sep. 7, 2011, 1 page.

Gopinath et al., "An RNA aptamer that distinguishes between closely related human influenza viruses and inhibits haemagglutinin-mediated membrane fusion," *J. Gen. Virol.* vol. 87, pp. 479-487, 2006.

Hou et al., "Building Bio-Inspired Artificial Functional Nanochannels: From Symmetric to Asymmetric Modification," *Angew. Chem. Int. Ed.*, vol. 51, pp. 5296-5307, 2012.

Perez-Mitta et al., "Bioinspired integrated nanosystems based on solidstate nanopores: "iontronic" transduction of biological, chemical and physical stimuli," *Chemical Science*, vol. 8, pp. 890-913, 2017.

Perez-Mitta et al., "Highly Sensitive Biosensing with Solid-State Nanopores Displaying Enzymatically Reconfigurable Rectification Properties," *Nano Lett.*, vol. 18, pp. 3303-3310, 2018.

* cited by examiner

FIG. 1A

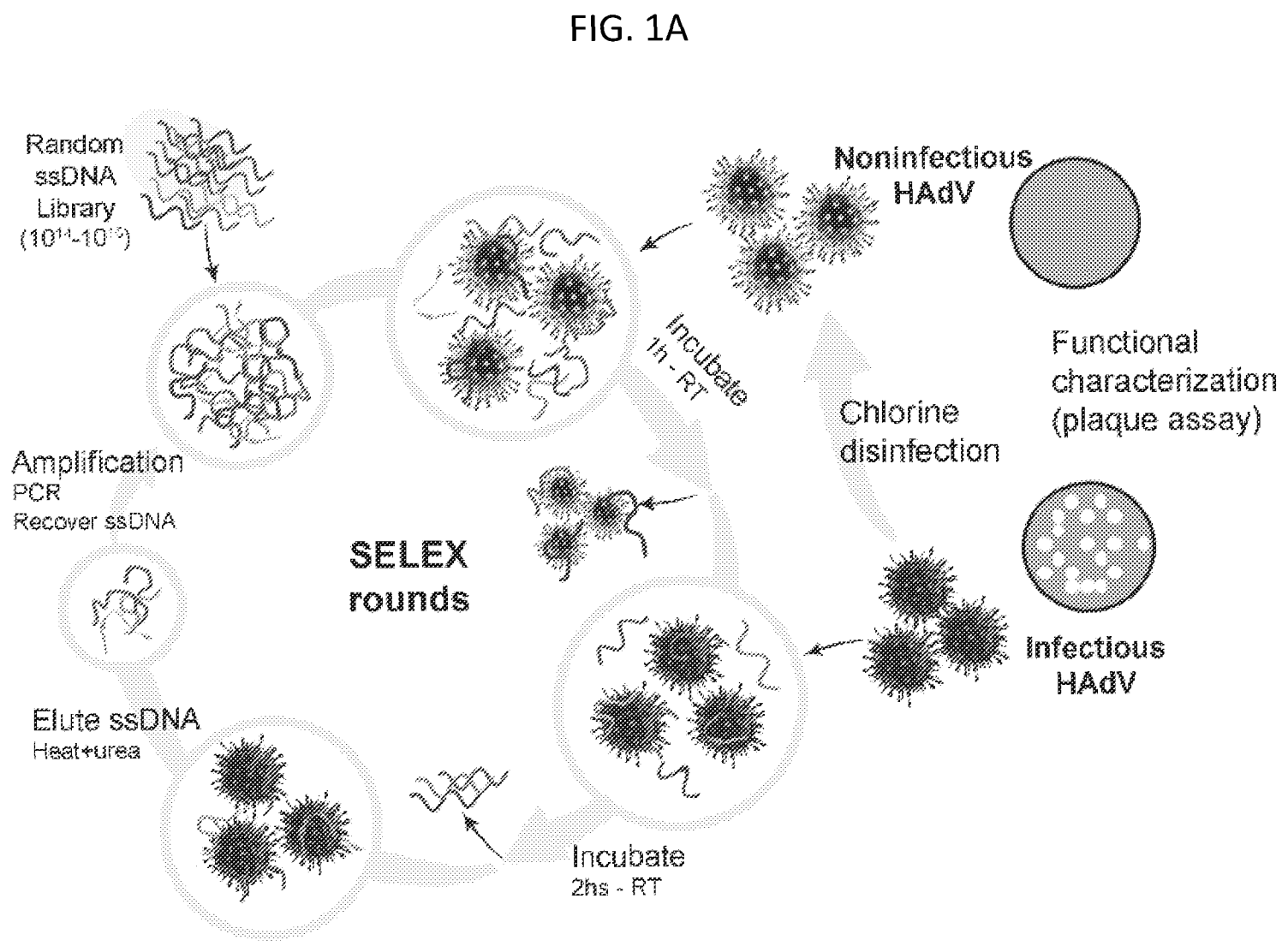

Random ssDNA Library ($10^{14}$-$10^{15}$)
Amplification
PCR
Recover ssDNA
Elute ssDNA
Heat+urea
SELEX rounds
Incubate
1h - RT
Incubate
2hs - RT
Noninfectious HAdV
Chlorine disinfection
Infectious HAdV
Functional characterization (plaque assay)

Elution yield
Round

-dF/dT
Temperature (°C)

b
Affinity assay
Infectious virus
Kd= 0.9 ± 0.1 nM
Noninfectious virus
Absorbance at 450nm
C aptamer (nM)

Reads per millon 0
2
4
6
8

2 3 4 5 6 7 8 9 10 11

Round

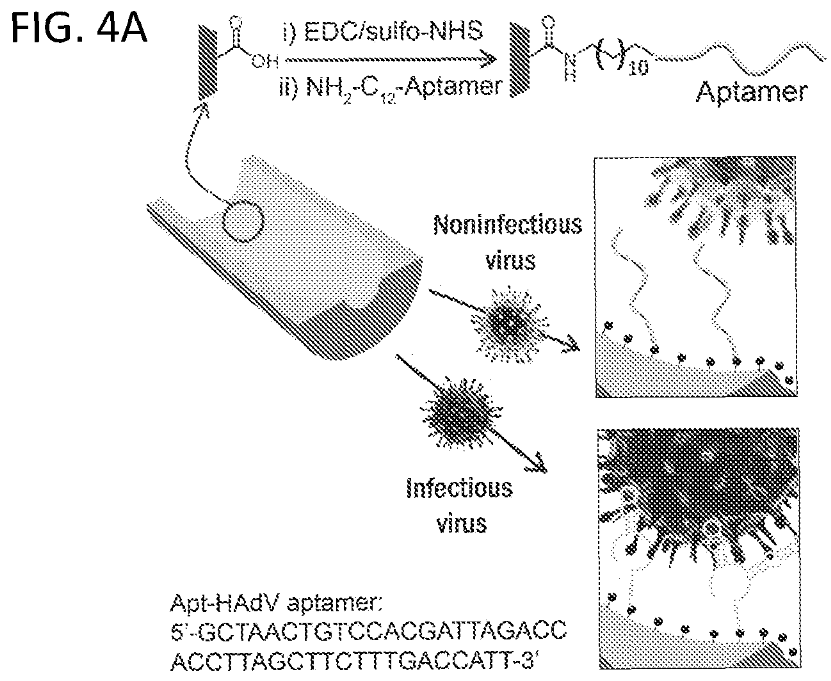
FIG. 4A
i) EDC/sulfo-NHS
ii) NH2-C12-Aptamer
Aptamer
Noninfectious virus
Infectious virus
Apt-HAdV aptamer:
5'-GCTAACTGTCCACGATTAGACC
ACCTTAGCTTCTTTGACCATT-3'
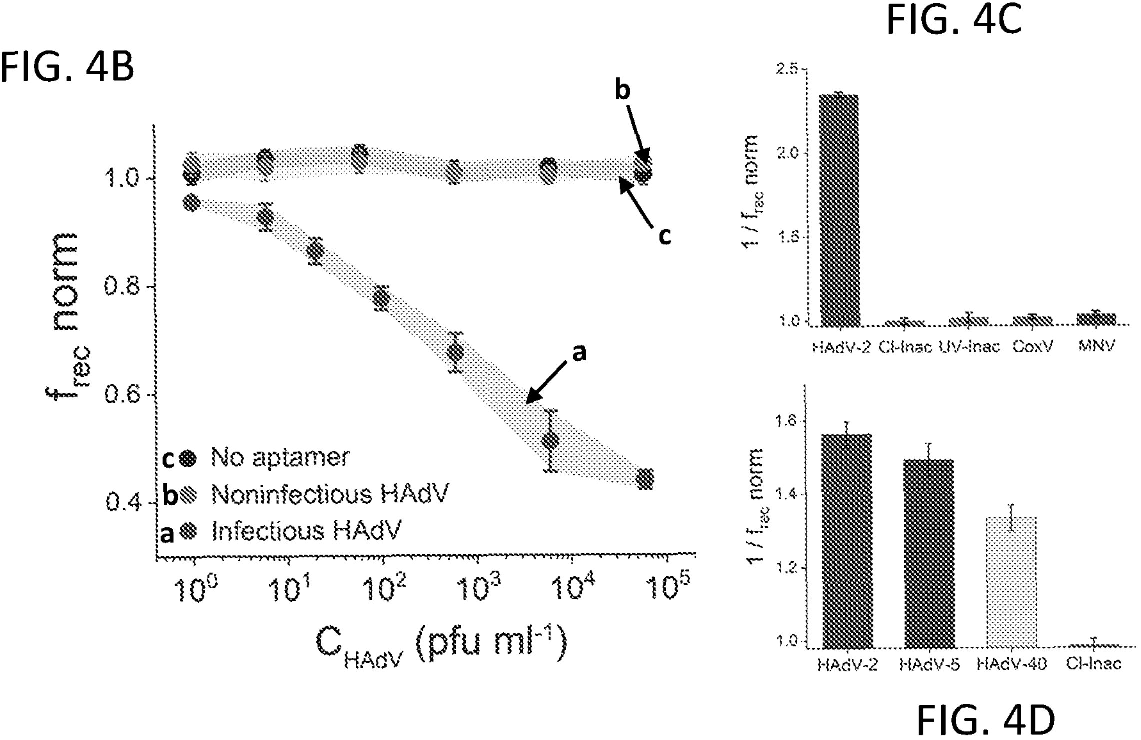
FIG. 4B
FIG. 4C
FIG. 4D
f_rec norm
C_HAdV (pfu ml^-1)
c No aptamer
b Noninfectious HAdV
a Infectious HAdV
1 / f_rec norm
HAdV-2
Cl-inac
UV-inac
CoxV
MNV
HAdV-5
HAdV-40

Measure reference I-V curve
Sample without pretreatment:
Buffer
Environmental water
Human serum and saliva
Incubation 30min - RT
Wash
Measure I-V curve
Inactivation percentages in buffer
99.9%
99%
90%
C i-HAdV - nanopore
C i-HAdV - plaque assay
$10^1$
$10^2$
$10^3$ Borehole water
Tap water
Wastewater Saliva
Serum

FIG. 13

$f_{rec}norm$ 1.1
1.0
0.9
0.8
0.7
0.0 a
b
c
d buffer
Tap water
Borehole water
Waste water i (nA)
20
10
0
c Buffer
b Human serum
a Human serum + 60pfu/ml i-HAdV
c
b
a
-1.0
-0.5
0.0
0.5
1.0
transmembrane potential (V)

i (nA)
60
40
20
0
c Buffer
b Saliva
a Saliva + 60pfu/ml i-HAdV
c
b
a
-1.0
-0.5
0.0
0.5
1.0
transmembrane potential (V)
$f_{rec}$norm
1.0
0.9
0.8
0.7
0.6
0.0
a Serum
b Saliva
6
60
600
$C_{i\text{-}HAdV}$ (pfu ml$^{-1}$)

$C_{i\text{-}HAdV}$ - nanopore (pfu/ml)
Serum
Saliva
6pfu/ml
60pfu/ml
600pfu/ml
$C_{i\text{-}HAdV}$ - plaque assay pseudotyped SARS-CoV-2
Kd= 4.8x10^5 copies/ml
F_norm (%)
C_p-SARS-CoV-2 (copies/ml)

UV-inactivated pseudotyped SARS-CoV-2
F_norm (%)
C_UV-p-SARS-CoV-2 (copies/ml)
229E coronavirus
F_norm (%)
C_229E coronavirus (copies/ml)
pseudotyped SARS-CoV-1
F_norm (%)
C_p-SARS-CoV-1 (copies/ml)
pseudotyped H5N1
F_norm (%)
C_p-H5N1 (copies/ml)

METHODS AND COMPOSITIONS FOR RAPID DIRECT DETECTION AND DIFFERENTIATION OF INFECTIOUS FROM NONINFECTIOUS VIRUS

CROSS REFERENCE TO RELATED APPLICATION

This application is the § 371 U.S. National Stage of International Application No. PCT/US2021/033245, filed May 19, 2021, which was published in English under PCT Article 21 (2), which in turn claims the benefit of U.S. Provisional Application No. 63/027,799, filed May 20, 2020, which is incorporated herein by reference in its entirety.

GOVERNMENT SUPPORT CLAUSE

This invention was made with government support under 2029215 awarded by The National Science Foundation. The United States Government has certain rights in the invention.

SEQUENCE LISTING INCORPORATION BY REFERENCE

The Sequence Listing is submitted as an ASCII text file in the form of the file named 7950-104523-03_ST25.txt, which was created on Nov. 18, 2022, and is 3,388 bytes, which is incorporated by reference herein.

FIELD

This disclosure relates to methods and compositions for detecting viruses utilizing one or more virus-specific aptamers, particularly for differentiating infectious and non-infectious viruses.

BACKGROUND

Viral infections are an increasingly important public health issue, as viral outbreaks have resulted in enormous economic and societal impact around the world. Critical to address this issue is rapid, portable, and accurate detection and quantification of viruses with high sensitivity and selectivity, preferably down to one infectious virion within the entire sample being assessed, because timely and accurate diagnosis is paramount in treating viral infections while preventing the spread of viruses to healthy people.

Toward this goal, many methods have been developed to detect and quantify viruses. Microbiology techniques, such as plaque assay, have been a standard method for many years. However, it takes several days to grow plaques, making it difficult for on-site and real-time detection. In addition, virus propagation requires growing their host cells, increasing the required labor, expertise, and equipment and is not suitable for viruses that do not replicate well in cell culture systems. To overcome these limitations, qPCR has been developed for rapid virus detection. However, portable detection using PCR has been difficult to commercialize due to the need for sample pretreatment and the occurrence of sample cross-contamination, the latter resulting in false positive or false negative results. Other recently developed portable methods based on nucleic acid detection, like SHERLOCK (Gootenberg et al., *Science* 356:438-442, 2017; Gootenberg et al., *Science* 360:439-444, 2018; Myhrvold et al., *Science* 360:444-448, 2018), are markedly powerful for diagnostic applications. However, because they are based on detection of nucleic acids inside the viruses, they still require sample pretreatment to extract nucleic acids from the virions for detection. More importantly, no methods have been reported to be able to differentiate infectious from noninfectious viruses in a direct and rapid manner, which is critical in preventing false positive results. The only available alternative is to combine cell culture, enzymatic treatments or immunoassay with PCR, resulting in time consuming and extended sample preparation methods (Hamza et al., *J. Virol. Methods* 266:11-24, 2019).

SUMMARY

Available methods currently do not meet the needs for viral detection and differentiation, causing delays and misdiagnoses. Disclosed herein are sensors and methods for rapid detection of viruses and for differentiation of infectious from noninfectious virus in a variety of sample types, including drinking water, waste water effluent, and serum samples, with little or no pretreatment of the environmental or biological samples, by integrating a highly selective nucleic acid aptamer with a highly sensitive solid-state nanopore. In some examples, the differentiation of infectious from noninfectious virus can be made at a single viral particle level.

In some embodiments, methods of detecting presence of a virus in a sample are provided, the methods including contacting the sample with a solid state nanopore comprising a plurality of covalently attached virus-specific nucleic acid aptamers and measuring a current-voltage curve in the solid state nanopore, wherein a decrease in the current indicates presence of the virus in the sample. In some examples, the solid state nanopore is formed through a membrane and the membrane is present in a reservoir, wherein the reservoir is separated into two compartments by the membrane, and the current-voltage curve is measured using two or more electrodes. In particular examples, the plurality of aptamers are covalently attached to the inner wall of the solid state nanopore.

In some embodiments, the aptamer specifically binds to an intact virus particle. In particular examples, the intact virus particle is an infectious virus. In other examples, the aptamer does not bind a non-infectious virus particle. In particular examples, the nucleic acid aptamer is a DNA aptamer. In some examples, the virus is a human adenovirus. In a particular non-limiting example, the DNA aptamer comprises or consists of the nucleic acid sequence of SEQ ID NO: 5. In other examples, the virus is a coronavirus, for example, SARS-CoV-2. In a particular non-limiting example, the DNA aptamer comprises or consists of the nucleic acid sequence of SEQ ID NO: 11.

In additional embodiments the method detects $10^4$ pfu/ml or less of virus in a sample (for example, $10^3$ pfu/ml or less, $10^2$ pfu/ml or less, 10 pfu/ml or less, or 1 pfu/ml or less of virus). In other examples, the method detects a single virus particle in a sample.

The sample includes any sample that contains or is suspected to contain a virus, such as a biological specimen (for example, blood, serum, plasma, bronchoalveolar lavage, a nasopharyngeal swab, an oropharyngeal swab, saliva, or sputum) or an environmental specimen (for example, a water sample or surface swab). In some embodiments, the sample is resuspended or diluted in water or buffer prior to contacting with the solid state nanopore comprising the aptamer. In particular examples, resuspending or diluting the sample is the only sample processing step prior to use in the disclosed methods. In other examples, the sample is used directly, without processing.

Also provided herein are solid state nanopores comprising a plurality of virus-specific nucleic acid aptamers covalently linked to the interior of the solid state nanopore. In some embodiments, the solid state nanopore passes from a first surface to a second surface of a membrane (such as a polyethylene terephthalate membrane). In some examples, the nucleic acid aptamer includes a 5' or 3' modification (such as an amine modification) to facilitate covalent linkage of the aptamer to the solid state nanopore. In some examples, the aptamer also includes a spacer (such as a carbon spacer) between the aptamer and the 5' or 3' modification.

In some embodiments, the aptamer covalently linked to the solid state nanopore specifically binds to an intact virus particle, such as an infectious virus particle. In other examples, the aptamer covalently linked to the solid state nanopore does not bind to a non-infectious (e.g., inactive) virus particle. In particular examples, the nucleic acid aptamer is a DNA aptamer. In some examples, the virus is a human adenovirus. In a particular non-limiting example, the DNA aptamer comprises or consists of the nucleic acid sequence of SEQ ID NO: 5. In other examples, the virus is a coronavirus, for example, SARS-CoV-2. In a particular non-limiting example, the DNA aptamer comprises or consists of the nucleic acid sequence of SEQ ID NO: 11.

Also provided herein are membranes including a plurality of solid state nanopores, each solid state nanopore including a plurality of covalently attached virus-specific nucleic acid aptamers. In some embodiments, kits comprising a membrane including a plurality of solid state nanopores each including a plurality of covalently attached virus-specific nucleic acid aptamers are also provided. The kits may further include one or more reagents and/or instructions for use. Also provided are systems that include one or more membranes including the solid state nanopore/aptamer sensors disclosed herein and one or more electrodes that are electrically coupled to the membrane. In some embodiments, the system includes at least 1, 2, 3, or 4 electrodes.

The foregoing and other features of the disclosure will become more apparent from the following detailed description, which proceeds with reference to the accompanying figures.

BRIEF DESCRIPTION OF THE DRAWINGS

FIGS. 1A-1D illustrate in-vitro selection of infectious adenovirus-specific aptamer. FIG. 1A is a schematic representation of an exemplary in-vitro selection process for a human adenovirus (HAdV) aptamer. Positive and counter selections steps were added in each round to reach high specificity toward infectious virus. FIG. 1B is a graph monitoring the progress of SELEX process by quantification of the elution yield, as the bound ssDNA over the added ssDNA, using qPCR. FIG. 1C shows melting curves for the different pools during HAdV aptamer (Apt-HAdV) selection. After round 3, a peak at higher melting temperature ($T_m$) appeared and shifted from 82° C. in the middle rounds to 85° C. until round 7 where its intensity increased, suggesting that the DNA pool converged from mostly random sequences with low $T_m$ to more conserved sequences with higher $T_m$. FIG. 1D shows binding curves obtained from the ELONA assay. The dissociation constant ($K_d$) of Apt-HAdV sequence for the infectious HAdV (0.9 nM) was more than 100 times higher than for noninfectious HAdV. n=3 technical replicates (mean±SD).

FIG. 2B). Calculations were made at 25° C., 100 mM NaCl and 2 mM $MgCl_2$.

FIG. 3A shows from left to right, for infectious HAdV: TFA melt curves; difference of the melt curve between 0 pfu/ml virus and different concentrations of HAdV; and binding curve at 67° C. in presence of 20 nM of Apt-HAdV aptamer based on triplicate data. The peak around 67° C. changed with different concentrations of infectious HAdV, compared with the aptamer solution that does not contain the virus (buffer only, black line). Then, the change in the signal at 67° C. was used to obtain the binding curve, by subtracting the signal without the virus, $(dF/dT)_{buffer}$, and the signal with different concentration of virus, $(dF/dT)_{virus}$. FIG. 3B shows the same melt curves as FIG. 3A, but for non-infectious HAdV. In this case, no significant change was observed at 67° C. or other temperature. FIG. 3C is TFA melt curves for different blanks tested: infectious HAdV without DNA (left), infectious HAdV with 20 nM of a random sequence with the same length of the Apt-HAdV aptamer (middle), and coxsackie virus with 20 nM of Apt-HAdV aptamer (right).

FIGS. 4A-4D show infectious virus detection using aptamer-functionalized nanopore sensors. FIG. 4A is a schematic depicting an exemplary modification of the nanopore and the interaction of the Apt-HAdV aptamer (SEQ ID NO: 5) with infectious HAdV samples. FIG. 4B shows normalized rectification efficiencies ($f_{rec}$norm) versus virus concentration. n=3, technical replicates (mean±SD). When no aptamer was added on the nanopore, no change in the $f_{rec}$norm was observed for infectious HAdV. The nanopore modified with $NH_2$-$C_{12}$-aptamer for different concentrations of noninfectious virus and infectious virus are also shown. FIG. 4C shows selectivity assay. Inverse of the $f_{rec}$norm obtained for infectious HAdV (HAdV-2), two noninfectious HAdVs using different inactivation mechanisms: free chlorine (Cl-inact) and UV-light (UV-inact), and two other viruses: Coxsackievirus B5 (CoxV) and Murine Norovirus (MNV). The concentration of each virus is $5\times10^4$ pfu/mL. FIG. 4D shows inverse of the $f_{rec}$norm obtained for different serotypes of infectious adenovirus (HAdV-2, HAdV-5 and HAdV-40) and comparison with an inactivated-HAdV sample at the same concentration ($1\times10^3$ pfu/mL).

FIG. 8A shows a scheme of infectious HAdV detection by the aptamer-nanopore system. FIG. 8B shows quantification of infectious HAdV in a mixture of infectious and noninfectious HAdV by comparison of aptamer-nanopore sensor (y-axis) with plaque assay (x-axis). FIG. 8C shows quantification of infectious HAdV in different real water samples without any pretreatment or dilution by comparison of aptamer-nanopore sensor (y-axis) with plaque assay (x-axis). FIG. 8D is quantification of infectious HAdV in human serum and saliva without dilution of the biological sample by comparison of aptamer-nanopore sensor (y-axis) with plaque assay (x-axis). n=3, technical replicates (mean±SD).

FIG. 13 is a graph showing normalized rectification efficiency obtained for different water samples in present of non HAdV (gray) and in a solution of HAdV with 99.9% inactivation (mixture of infectious and non-infectious viruses).

FIG. 14A shows I-V curves for a human serum sample before and after being spiked with 60 pfu/mL infectious HAdV. There was a change in the I-V curve when the nanopore was incubated in human serum compared with the curve after incubation with buffer. To take these differences into account, the $f_{rec}$ for the human serum samples with different concentrations of infectious HAdV were normalized by the measurement after incubation in human serum, instead of buffer. FIG. 14B shows I-V curves for a human saliva sample before (dark) and after (light) being spiked with 60 pfu/mL infectious HAdV. FIG. 14C is a graph of normalized rectification efficiency obtained for human serum and saliva samples spiked with different concentrations of infectious HAdV. n=3, technical replicates (mean±SD). FIG. 14D shows individual values for each concentration (triplicate) for different biological samples.

FIG. 16A shows normalized rectification factor versus logarithm of the infectious HAdV concentration after 30 min incubation of the virus solution with the aptamer-nanopore without stirring or with magnetic stirring. FIG. 16B shows relative change of the $f_{rec}$norm (defined as the percent change of 1-$f_{rec}$norm) when stirring is added compared with the relative $f_{rec}$norm without stirring, for different concentrations of infectious HAdV. The larger changes were observed for lower infectious HAdV concentrations, and at 600 pfu/mL, no significant changes were observed.

FIG. 18A is a plot monitoring the progress of SELEX process by quantification of the elution yield, the bound ssDNA over the added ssDNA, using qPCR. FIG. 18B shows melting curves for the different pools during SARS-CoV-2 aptamer selection. The peak at high Tm shifted from 77° C. to 79° C., suggesting that the DNA pool converged from random sequences with low Tm to more conserved sequences with higher Tm. FIG. 18C shows reads per millions (RPM) obtained by analysis of the HTS data for SARS2-AR10 sequence as a function of the selection rounds, using FASTAptamer-Count.

FIG. 22A shows normalized rectification efficiencies versus virus concentration. n=2, technical replicates. FIG. 22B shows selectivity assay. Inverse of the $f_{rec}$norm obtained for active pseudotyped SARS-CoV-2 (SARS-2), UV-inactivated pseudotyped SARS-CoV-2 samples (UV-SARS-2); another coronavirus: 229E, and two other pseudoviruses: SARS-CoV-1 (SARS-1) and influenza virus (H5N1). The concentration of each virus is $1\times10^6$ copies/mL. FIG. 22C is a comparison of aptamer-nanopore sensor (y-axis) with luciferase assay (x-axis) to quantify active pseudotyped SARS-CoV-2 in human saliva without dilution of the biological sample. n=3, technical replicates (mean±SD). Each of these measurements was performed with a new membrane.

SEQUENCE LISTING

Figures 1B, 1C, 1D:
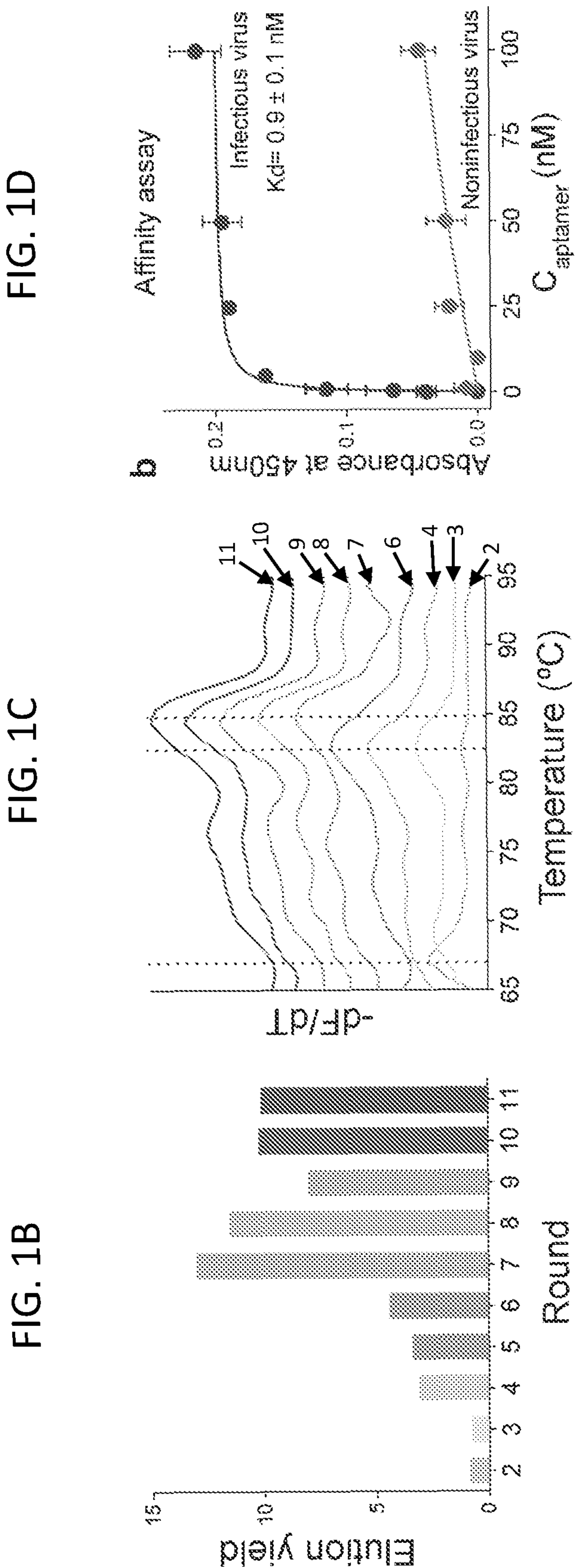

Any nucleic acid and amino acid sequences listed herein or in the accompanying Sequence Listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NO: 1 is the nucleic acid sequence of a DNA library oligonucleotide used to generate an HAdV aptamer.

SEQ ID NOs: 2 and 3 are forward and reverse primers for amplification of the HAdV aptamer, NGS preparation, and qPCR quantification.

SEQ ID NO: 4 is a T20 oligonucleotide.

SEQ ID NO: 5 is the nucleic acid sequence of an exemplary HAdV aptamer.

SEQ ID NOs: 6 and 7 are 5'- and 3'-modified HAdV aptamers, respectively.

SEQ ID NO: 8 is the nucleic acid sequence of a DNA library oligonucleotide used to generate a SARS-CoV-2 aptamer.

SEQ ID NOs: 9 and 10 are forward and reverse primers for amplification of the SARS-CoV-2 aptamer, NGS preparation, and qPCR quantification.

SEQ ID NO: 11 is the nucleic acid sequence of an exemplary SARS-CoV-2 aptamer (SARS2-AR10).

SEQ ID NO: 12 is a 5'-modified SARS-CoV-2 aptamer.

DETAILED DESCRIPTION

Described herein are aptamer-nanopore systems that can rapidly differentiate infectious from noninfectious viruses, with a detection limit down to 1 pfu/ml demonstrated. This sensitivity rivals those for standard viral assay methods such as plaque assay and qPCR techniques. The disclosed systems and methods are rapid, providing results in as little as 30 minutes, as well as being highly sensitive and specific (including the ability to discriminate infectious vs. non-infectious virus). Furthermore, as described herein the method can detect infectious viruses that cannot replicate well in cell culture system (such as HAdV-40), and are thus not readily detectable by the standard plaque assay, which require replication in cell culture. In addition, the disclosed system and methods can detect intact viruses directly in samples, for example, with little or no pre-processing, and without the need to collect and disrupt the viruses for nucleic acid extraction, as required for PCR. Finally, since SELEX does not depend on known biomarkers the disclosed methods and sensors can be readily applied to obtain aptamers for many other infectious viruses, including new emerging viruses.

I. Terms

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, 3rd Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. "Comprising A or B" means including A, or B, or A and B.

Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Aptamer: An oligonucleotide or peptide molecule that binds to a specific target of interest. In some examples herein, aptamers are short, single-stranded DNA or RNA (ssDNA or ssRNA) molecules that can selectively bind to a specific target, including proteins, peptides, carbohydrates, small molecules, toxins, cells, and/or viruses. Aptamers can assume a variety of shapes due to their tendency to form secondary structures, such as helices and single-stranded loops (for example, a hairpin). In specific examples, an aptamer is coupled to a nanopore, such as a solid state nanopore.

Linkage: Coupling or conjugation of two molecules, for example by a covalent bond. Direct linkage is coupling or conjugation without an intervening linker between the two molecules. Indirect linkage is coupling or conjugation with an intervening linker between the two molecules. In some examples, a direct linkage is formed when an atom of a first molecule (such as a DNA aptamer) bonds to an atom of a second molecule (such as a solid state nanopore). In other examples, an indirect linkage includes one or more functional groups between the first molecule (such as a DNA aptamer) and the second molecule (such as a solid state nanopore).

Nanopore: A pore, channel, gap, conduit, or groove in a membrane or layer and passing therethrough (e.g., from a first surface of the membrane or layer to a second surface of the membrane or layer), where the pore, channel, gap, conduit, or groove is a nanometer-sized opening. A solid state nanopore is a non-biological pore (e.g., is not a nanopore formed by one or more protein subunits) that be used as a detector to measure a change in current flowing through the pore caused by partial blockade of the pore by an object (such as a virus particle) as it passes through.

Sample: As used herein, a sample includes biological or environmental specimens useful for detecting a virus. Biological specimens include, but are not limited to, cells, tissues, and bodily fluids, such as blood; derivatives and fractions of blood, such as serum; extracted galls; biopsied or surgically removed tissue, including tissues that are, for example, unfixed, frozen, fixed in formalin, and/or embedded in paraffin; autopsy material; tears; milk; skin scrapes; surface washings; urine; sputum; cerebrospinal fluid; pus; bone marrow aspirates; middle ear fluids; bronchoalveolar lavage; tracheal aspirates; nasopharyngeal aspirates or swabs; oropharyngeal aspirates or swabs; or saliva. Environmental samples, include for example, food, water (such as water from wells, domestic water systems, municipal water systems, fountains, or bodies of water (such as lakes, creeks, rivers, etc.)), soil, surface swabs, or other materials that may contain or be contaminated with a virus.

Specifically binds: The binding of an agent that preferentially binds or substantially only binds to a defined target (such as a DNA aptamer to a specific virus). Specific binding may refer to binding of a DNA aptamer to a specific class of viruses, a specific genotype or serotype of a virus, or an infectious virus (as opposed to a non-infectious or inactive virus).

Subject: A living multi-cellular vertebrate organism, a category that includes but is not limited to human and non-human mammals.

II. Solid State Nanopore/Aptamer Sensors

Provided herein are sensors that include at least one aptamer (such as a virus-specific aptamer) covalently attached to a solid state nanopore. In particular embodiments, the sensor is a solid state nanopore including a plurality of virus-specific nucleic acid aptamers each covalently linked to the solid state nanopore.

The aptamers incorporated in the sensors and utilized in the methods described herein are selected to specifically bind a virus of interest, and in some examples to specifically bind to an infectious virus but not to a non-infectious virus (e.g., a virus that is not capable of causing infection, such as an inactivated virus). In some embodiments provided herein, the aptamer is a DNA aptamer. In some examples, the DNA aptamer is an L-DNA aptamer or includes one or more modified nucleotides or backbone modifications (e.g., phosphorothioates, phosphoramidates, base modifications, peptide nucleic acids or locked nucleic acids). In other examples, the aptamer is an RNA aptamer.

In particular embodiments, the virus-specific aptamer is obtained by an in vitro selection process (e.g., systematic evolution of ligands by exponential enrichment (SELEX)). In some examples, the selection includes positive selection for a virus of interest (e.g., a human adenovirus or a coronavirus), which may be an infectious virus. In additional examples, the selection also includes a counter-selection with non-infectious virus, such as the virus of interest that has been inactivated (e.g., by ultraviolet light or chemical treatment). An exemplary selection method is described in the Examples below, and is shown schematically in FIG. 1A. This method is illustrated herein with HAdV, but can be used for any virus of interest to develop a DNA aptamer for incorporation into the methods and sensors described herein.

Exemplary viruses for which an aptamer (such as a DNA or RNA aptamer) can be developed include, but are not limited to adenovirus, coronavirus (e.g., alpha coronavirus, beta coronavirus (such as MERS-CoV, SARS-CoV, or SARS-CoV-2), gamma coronavirus, or delta coronavirus), coxsackievirus, norovirus, human immunodeficiency virus (HIV), polio virus, hepatitis A virus, hepatitis B virus, hepatitis C virus, enterovirus, rhinovirus, echovirus, foot-and-mouth disease virus, Norwalk virus, chikungunya virus, equine encephalitis virus, Simliki Forest virus, Sindbis virus, Ross River virus, rubella virus, dengue virus, yellow fever virus, West Nile virus, St. Louis encephalitis virus, Japanese encephalitis virus, Powassan virus, Zika virus, rabies viruses, Ebola virus, Marburg virus, parainfluenza virus, mumps virus, measles virus, respiratory syncytial virus, influenza virus, papilloma virus, polyoma viruses, herpes simplex virus, cytomegalovirus, Epstein-Barr virus, varicella zoster virus, hantavirus, and others.

In some embodiments provided herein, the aptamer specifically binds to a human adenovirus (e.g., binds to a human adenovirus, but does not appreciably bind to other viruses). In some examples, the aptamer specifically binds to a single HAdV serotype (e.g., binds to one HAdV serotype but does not appreciably bind to other HAdV serotypes), while in other examples, the aptamer specifically binds to two or more HAdV serotypes. In one non-limiting example, the aptamer binds to one or more of HAdV-2, HAdV-5, and HAdV-40. In additional examples, the aptamer specifically binds to an infectious human adenovirus (e.g., binds to a human adenovirus capable of causing infection), but does not appreciably bind to a human adenovirus that is not capable of causing infection (such as an inactivated human adenovirus). In a specific, non-limiting example, the aptamer includes or consists of the nucleic acid sequence of SEQ ID NO: 5.

In other embodiments provided herein, the aptamer specifically binds to a coronavirus (e.g., binds to a coronavirus, but does not appreciably bind to other viruses). In some examples, the aptamer specifically binds to a single coronavirus species (e.g., binds to one coronavirus species but does not appreciably bind to other coronavirus species), while in other examples, the aptamer specifically binds to two or more coronavirus species. In one non-limiting example, the aptamer binds to SARS-CoV-2. In additional examples, the aptamer specifically binds to an infectious coronavirus (e.g., binds to a coronavirus capable of causing infection), but does not appreciably bind to a coronavirus that is not capable of causing infection (such as an inactivated coronavirus). In a specific, non-limiting example, the aptamer includes or consists of the nucleic acid sequence of SEQ ID NO: 11.

The solid state nanopore is a nanometer-sized pore or channel formed in a solid state layer such as a non-biological sheet or membrane. The nanopore passes from a first surface of the layer to a second surface of the layer, such as a first surface of a membrane to a second surface of a membrane. The layer is some examples is made of organic and/or inorganic materials which include polymers, glass, $Si_3N_4$, Au—$Si_3N_4$, or graphene. Exemplary polymers include polyethylene-terephthalate (PET), polycarbonate, polyimide, and block copolymers. The membrane structure may include one or more nanopores, which may be arranged in an addressable configuration. In some examples, the membrane includes at least one nanopore/$cm^2$, such as 1-10 nanopores/$cm^2$, 10-100 nanopores/$cm^2$, $10^2$-$10^3$ nanopores/$cm^2$, $10^3$-

$10^4$ nanopores/cm$^2$, $10^4$-$10^5$ nanopores/cm$^2$, $10^5$-$10^6$ nanopores/cm$^2$, $10^6$-$10^7$ nanopores/cm$^2$, $10^7$-$10^8$ nanopores/cm$^2$, $10^8$-$10^9$ nanopores/cm$^2$, or $10^9$-$10^{10}$ nanopores/cm$^2$.

In some embodiments, the solid state nanopore has a circular cross-section. In some examples, the diameter of the solid state nanopore (such as at least a portion of the solid state nanopore) is about 5-2000 nm, for example about 5-25 nm, about 20-50 nm, about 50-100 nm, about 100-300 nm, about 200-500 nm, about 400-600 nm, about 500-800 nm, about 700-900 nm, about 800-1000 nm, about 1000-1200 nm, about 1200-1500 nm, about 1400-1800 nm, or about 1600-2000 nm. In other embodiments, the solid state nanopore has a tapered or bullet-like (e.g., a combination of longer cylindrical and shorter parabolic segments) cross-section, for example where the diameter of the solid state nanopore is different at the first surface of the membrane than the diameter of the solid state nanopore at the second surface of the membrane. In some examples, the diameter of the solid state nanopore at the first surface of the membrane is about 8-200 nm, for example, about 8 nm, about 10 nm, about 20 nm, about 30 nm, about 40 nm, about 50 nm, about 55 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, or about 200 nm, for example, about 8-20 nm, about 10-50 nm, about 50-60 nm, about 30-60 nm, about 40-80 nm, about 70-100 nm, about 90-120 nm, about 110-150 nm, about 130-160 nm, about 140-180 nm, or about 170-200 nm. In other examples, the diameter of the solid state nanopore at the second surface of the membrane is about 200-2000 nm, for example, about 200 nm, about 300 nm, about 400 nm, about 500 nm, about 600 nm, about 700 nm, about 800 nm, about 900 nm, about 1000 nm, about 1100 nm, about 1200 nm, about 1300 nm, about 1400 nm, about 1500 nm, about 1600 nm, about 1700 nm, about 1800 nm, about 1900 nm, or about 2000 nm, such as about 200-500 nm, about 300-700 nm, about 400-800 nm, about 800-1000 nm, about 900-1200 nm, about 1200-1500 nm, about 1300-1700 nm, about 1400-1800 nm, or about 1700-2000 nm. In one non-limiting example, the solid state nanopore has a diameter of about 50-60 nm at the first surface of the membrane and a diameter of about 800-1000 nm at the second surface of the membrane. In additional examples, the nanopore is cylindrical, conical, bullet-shaped, symmetric double conical, or cigar-shaped. See e.g., Hou et al., *Angew. Chem. Int. Ed.* 51:5296-5307, 2012. *In additional embodiments, the length of the solid state nanopore is about* 5-50 μm (such as about 5-15 μm, about 10-20 μm, about 15-30 μm, about 25-40 μm, or about 30-50 μm). In one non-limiting example, the length of the nanopore is about 12 μm.

In embodiments of the disclosed sensors, the aptamer is covalently attached (e.g., coupled or linked) to the nanopore, for example, covalently attached to the inner wall of the nanopore. In some examples, the aptamer is directly or indirectly linked to the nanopore. In one example, the aptamer includes an amino modification at the 5' or the 3' end. In particular examples, the aptamer includes a 5' amino modification or a 3' amino modification. Additional 5' or 3' modifications can be selected by one of ordinary skill in the art. In particular examples, a spacer is included between the aptamer and the 5' or 3' modification, such as a $C_3$-$C_{12}$ spacer (for example, a $C_3$ spacer, a $C_6$ spacer, or a $C_{12}$ spacer). In one non-limiting example, the modification is a 5' or 3' amino modification with a $C_6$ or $C_{12}$ spacer.

In some examples, the aptamer is covalently attached to the nanopore by an carbodiimide EDC/N-hydroxysulfosuccinimide (sulfo-NHS) linkage between a carboxylate group in the nanopore and an amino modified aptamer. Additional methods of modifying the nanopore to covalently attach an aptamer can be selected by one of ordinary skill in the art, depending on the type of solid state nanopore utilized. In some examples, the modification includes utilizing EDC and pentafluorophenol (PFP) to activate the surface followed by reaction with ethylenediamine. In other examples, SiNx nanopores are modified using triethoxysilane. In still further examples, a glass nanopore is modified by silanizing the glass surface in the pore with aldehyde methoxysilane, followed by attaching amino-terminated DNA aptamers to the aldehyde-terminated glass surface in sodium cyanoborohydride. In other examples, the nanopore includes modification based on self-assembly of functional thiol molecules (for example, thiol labeled aptamers) to form Au—S covalent bonds after the electroless deposition of gold onto the inner surface of the nanochannel. In another example, the method includes modification by self-assembly, which does not imply the use of covalent chemistries directly from the surface of the nanopore, but the charge of the surface stemming from the surface groups (net negative charge at low pH due to the carboxylate group). This characteristic can be used as a substrate for electrostatic layer-by-layer deposition of polymers with different charges. In a further example, the modification is based on plasma modification of polymer materials to produce large amounts of free radicals in the surface layer. The newly generated free radicals continue to react to form functional groups. In an additional example, the modification is with ion sputtering to create a metal layer, for instance, gold and/or platinum that can be modified by thiol chemisorption, or modification by electron-beam evaporation. See, e.g., Hou et al., *Angewandte Chemie* International Edition Vol. 51, DOI: 10.1002/anie.201104904, 2012. One of ordinary skill in the art can select an appropriate method of covalently linking the nucleic acid aptamer to a modified nanopore.

Also provided are systems that include one or more membranes including the solid state nanopore/aptamer sensors disclosed herein and one or more electrodes that are electrically coupled to the membrane. In some examples, the one or more electrodes are introduced in a solution that is in contact with the membrane. In some embodiments, the system includes at least 1, 2, 3, or 4 electrodes. In one non-limiting example, the system includes a membrane including the solid state nanopore/aptamer sensors disclosed herein, with a solution on each side of the membrane and one or more electrodes (such as 1 or 2 electrodes) placed in the solution on each side of the membrane. In additional embodiments, the system further includes one or more components for measuring and/or recording electrical current that are electrically connected to the electrodes, such as a potentiostat and a computer (which may be wirelessly connected to the potentiostat). In some examples, the computer is a smartphone. In further embodiments, the system also includes an amplifier and/or a digitizer.

Further contemplated herein are membranes and kits including the solid state nanopore/aptamer sensors disclosed herein. In some embodiments, the kit includes a membrane including one or more solid state nanopores including a plurality of covalently attached nucleic acid aptamers (such as a plurality of virus-specific aptamers). In some examples, the membrane includes a plurality of nanopores each including the same aptamers. In other examples, the membrane includes a plurality of nanopores wherein the aptamers included in at least two of the nanopores are different. In some examples, the kits further include one or more containers including some or all of the reagents (such as buffers) for carrying out methods of detecting a virus in a sample utilizing the solid state nanopore/aptamer sensors. In additional examples, instructions for use are also included.

III. Methods of Detecting Viruses

Methods of detecting presence of a virus in a sample utilizing an aptamer/solid state nanopore system are provided herein. The disclosed methods in some embodiments detect single virus particles. In some embodiments, the methods include determining whether a detected virus is an infectious or non-infectious virus.

In some embodiments, the methods include contacting a sample with a solid state nanopore comprising a plurality of virus-specific nucleic acid aptamers as described herein (e.g., Section II) and measuring a current-voltage curve in the solid state nanopore, wherein a decrease in the current indicates presence of the virus in the sample. In other examples, a decrease in normalized rectification efficiency ($f_{rec}$norm) indicates presence of virus in the sample. In some embodiments, the current-voltage curve is measured using electrophysiology techniques that are known to one of ordinary skill in the art. In particular examples, the solid state nanopore is formed through a membrane and the membrane is present in a reservoir, wherein the reservoir is separated into two compartments by the membrane, where the current-voltage curve across the membrane can be measured. Methods of measuring current-voltage (I-V) curves include using a potentiostat. In one example, the method includes utilizing a four-electrode set up (working, working sense, reference and counter-electrode) to monitor conductance variations arising from changes in the nanopore and which can be separated from other processes in solution or on electrode surfaces.

In particular embodiments, herein, the nanopore including the virus-specific aptamers has a larger diameter on one surface of the membrane than the other and the sample is incorporated in the compartment facing the larger diameter opening of the aptamer-modified nanochannel, and a buffer is included in the compartment facing the channel tip for measuring the I-V curve.

The disclosed methods have high sensitivity and specificity, as a result of the aptamer included in the solid state nanopore/aptamer sensor. In some examples, the method detects an intact virus particle, due to recognition and selective binding of intact virus particles by the aptamer. In further examples, the method specifically detects infectious virus particles. In still further examples, the method does not detect non-infectious virus particles. For example, the aptamer included in the solid state nanopore sensor specifically binds to intact, infectious virus particles, but does not bind to non-infectious virus particles (e.g., virus particles that are inactive or unable to cause an infection in a subject).

In some embodiments, the disclosed methods detect $10^4$ pfu/ml or less, $10^3$ pfu/ml or less, $10^2$ pfu/ml or less, 10 pfu/ml or less, or even 1 pfu/ml or less virus particles in a sample. In some examples, the methods may detect a single virus particle in a sample. As discussed above, depending on the aptamer used in the solid state nanopore sensor, the detected virus particles may be intact virus particles or may be infectious (not non-infectious) virus particles.

The methods described herein may be used for any purpose for which detection of a virus is desirable, such as in laboratory and clinical settings or environmental or other settings. Appropriate samples include any biological samples, including clinical samples obtained from a human or veterinary subject. Suitable samples include all biological samples useful for detection of viruses in subjects, including, but not limited to, cells (such as buccal cells or peripheral blood mononuclear cells), tissues, autopsy samples, bone marrow aspirates, bodily fluids (for example, blood, serum, plasma, urine, cerebrospinal fluid, tears, middle ear fluids, breast milk, bronchoalveolar lavage, tracheal aspirates, sputum, oral fluids, nasopharyngeal aspirates, oropharyngeal aspirates, or saliva), oral swabs, eye swabs, cervical swabs, vaginal swabs, rectal swabs, stool, and stool suspensions. Suitable samples also include environmental samples, for example, food, water (such as water from wells, boreholes, domestic or municipal water systems, wastewater processing plants, or bodies of water (such as lakes, creeks, rivers, etc.)), soil, air or aerosol samples (e.g., collected with a bioaerosol sampler, such as a NIOSH bioaerosol sampler connected to a pump), surface swabs, or other materials that may contain or be contaminated with a virus.

The sample can be used directly or can be processed, such as by adding solvents, preservatives, buffers, or other compounds or substances. In some examples, little or no pretreatment of the sample is carried out prior to use in the methods disclosed herein and the sample is used directly or with minimal pre-processing. For example, fluids can in some examples be diluted in water or buffer and used in the disclosed methods without additional processing. In other examples, samples can be processed by filtration or centrifugation to remove particles or debris. In one example, resuspending or diluting the sample is the only processing step prior to use of the sample in the methods described herein.

EXAMPLES

The following examples are provided to illustrate certain particular features and/or embodiments. These examples should not be construed to limit the disclosure to the particular features or embodiments described.

Example 1

Materials and Methods

Sample Preparation

DNA library: All the DNA sequences were purchased as synthetic oligonucleotides from Integrated DNA Technologies (IDT). A random ssDNA library (1 nmol) and reverse and forward primers were purified by polyacrylamide gel electrophoresis (PAGE).

The ssDNA pool consisted of a central random region of 45 nucleotides flanked by two constant sequences at the 3' and 5' ends that act as primer regions for amplification (Table 1). The reverse primer was modified with biotin to separate ssDNA from amplified double stranded PCR products using streptavidin-coated beads during the in-vitro selection process. Unmodified FwP and RevP were used for PCR amplification after the final round of the in vitro selection, for NGS libraries preparation and for qPCR quantification.

Proper folding of ssDNA library and pools was attained by denaturing at 95° C. for 10 minutes followed by cooling on ice for 10 min before use in each round.

TABLE 1

| HAdV DNA sequences | | |
|---|---|---|
| Name | DNA sequence (5' to 3') | SEQ ID NO: |
| DNA library HAdV | GTCCATCGTTCGGTAGTG(N)$_{45}$ GGCTAACTGTCCACGATT | 1 |
| Forward primer (FwP) HAdV | GTCCATCGTTCGGTAGTG | 2 |
| Reverse primer (RevP) HAdV | /**5Biosg**/AATCGTGGACAGTTAGCC | 3 |
| T20 | TTTTTTTTTTTTTTTTTTTT | 4 |
| Apt-HAdV | GGCTGCAGCTGAAGCACTGGTT TTGAGTCAAACCCAGACGATGGA | 5 |
| 3AmMO-Aptamer | GGCTGCAGCTGAAGCACTGGTTT TGAGTCAAACCCAGACGATGGA /**3AmMO**/ | 6 |
| $NH_2$—$C_{12}$-Aptamer | /**AmMC12**/GGCTGCAGCTGAAGC ACTGGTTTTGAGTCAAACCCAGA CGATGGA | 7 |

Modifications shown in bold type.
AmM = amino modification.
C12 = 12 carbon spacer.
5Biosg = biotin modification Virus Samples Human Adenovirus propagation and viability assessment: Human Adenovirus Serotype 2 (HAdV-2, VR-846) was propagated with A549 cells (CCL-185), both obtained from the American Type Culture Collection (Manassas, VA). Cell incubation, viral propagation and viral infectivity assessment methods were similar to previously reported protocols (Gall et al., *Environ. Sci. Technol.* 49:4584-4590, 2015; Sirikanchana et al., *Water Res.* 42:1467-1474, 2008). Briefly, A549 cell monolayers were maintained in flasks at 37° C. with 5% $CO_2$ with modified Ham's F12K media+10% fetal bovine serum+0.25 μg/ml amphotericin B+100 units/ml penicillin+10 μg/ml streptomycin (Sigma-Aldrich, St. Louis, MO). To propagate the viruses, HAdV-2 liquid stock was inoculated onto A549 cell monolayers and incubated at 37° C. with 5% $CO_2$ until cytopathic effects were observed. Viruses were released from the cells by freeze-thaw cycles. The lysates were centrifuged, and the supernatants were passed through 0.45 or 0.22 μm vacuum filters to remove large debris (Millipore, Billerica, MA). The filtrate was purified and concentrated using a 300 kDa ultrafiltration membrane (Millipore) in Amicon stirred cells. For some later batches of propagation, the filtrate was purified and concentrated using sucrose cushion ultracentrifugation. The concentrated virus stocks were in 1 mM carbonate buffer solution (CBS, Fisher Scientific) stored at −80° C. The virus infectivity was assessed with soft agar-overlay plaque assay and plaque counting at 9 or 10 days post infection were used to determine virus titers.

Inactivation of HAdV—Chlorine treatment: The inactivation of HAdV-2 by free chlorine was previously described (Page et al., *Water Res.* 43: 2916-2926, 2009; Gall et al., *Environ. Sci. Technol.* 49:4584-4590, 2015). In brief, a batch reactor with 1 mM CBS under continuous magnetic stirring was spiked with HAdV-2. The temperature was maintained with a constant temperature water bath, and pH was adjusted with hydraulic acid or sodium hydroxide solution. An initial sample was taken to measure initial viral concentration with the plaque assay method, and then sodium hypochlorite solution was added into the reactor while a timer was started at the same time. Samples were taken along with time and immediately mixed with 0.1% sodium thiosulfate to quench the chlorine and stop the inactivation process. The time points at which samples were added into sodium thiosulfate were recorded. Although the initial sample had no chlorine, it was also mixed with 0.1% sodium thiosulfate so that all the samples are comparable. The chlorine concentration was monitored with the N,N-diethyl-p-phenylene diamine (DPD) method (Rice et al., *Standard Methods for the Examination of Water and Wastewater* (American Public Health Association, ed. 23$^{rd}$, 2017)) and the sampling times and the chlorine concentrations were both recorded. Chlorine reacts extremely fast with viruses, leaving no time to measure the initial chlorine concentration in this reactor, so a second reactor controlling for the addition of virus stock was prepared in order to make the measurement of initial chlorine concentration possible.

The inactivated HAdV were dialyzed with 1 mM CBS buffer to remove the excess of sodium hypochlorite and sodium thiosulfate. In this way, the infectious and noninfectious HAdV are in the same buffer for the in vitro selection process.

Inactivation of HAdV-2 by low pressure ultraviolet light: The ultraviolet (UV) light inactivation experiments followed previously published methods except that a low-pressure UV lamp (GSL233T5L/SL, Atlantic Ultraviolet Corporation, Hauppauge, NY) was operated at 10 W and no band-pass filters were installed. A recirculating water-jacketed reactor (20° C.) containing 1 mM CBS was spiked with HAdV-2 under continuous magnetic stirring. The fluence was calculated as the product of the average irradiance and exposure time and four factors were measured for necessary corrections based on the literature (Bolton et al., *J. Environ. Eng.* 129:209-215, 2003). The irradiance distribution across the irradiated water surface was measured with a 1400A radiometer and SEL 240 detector (International Light, Peabody, Massachusetts) in order to correct for the nonuniformity of the light distribution (petri factor). The UV absorbance at 254 nm of the water sample to be treated by UV was measured with UV2700 Shimadzu spectrophotometer to adjust for water depth since UV can be absorbed by water (water factor). Distance of suspension from the UV lamp (divergence factor) and water surface reflection (reflection factor) were also considered into the calculation. With the average irradiance obtained and the desired fluence, the required exposure time was obtained.

Other viruses: Other viruses tested in this study include Human Adenovirus Serotype 5 (HAdV-5), Human Adenovirus Serotype 40 (HAdV-40), Coxsackievirus B5 and Murine Norovirus. HAdV-5 (VR-5) was obtained from ATCC and its propagation method and viral infectivity assessment are the same as those described for HAdV-2. HAdV-40 (Ad40, Dugan strain, p. 3, clone 6A) was obtained from Theresa Cromeans (Cromeans et al., *J. Virol. Methods* 151:140-145, 2008) (Centers for Disease Control and Prevention). Coxsackievirus B5 Faulkner (VR-185) was obtained from ATCC and passaged in buffalo green monkey kidney cell (QUIDEL, San Diego, CA) monolayers three times, and then purified and concentrated following the protocol of HAdV-2. Murine Norovirus was originally provided by Herbert Virgin (formerly at Washington University School of Medicine, St. Louis, MO) and propagated using RAW 264.7 cells (TIB-71) obtained from ATCC. The virus purification and concentration protocol were similar to those of HAdV-2.

Water samples and serum sample: Tap water was obtained from the tap at the University of Illinois at Urbana-Champaign, in Illinois, US. A more complex drinking water sample was obtained from a borehole at Panyodoli Secondary School in Kiryandongo District, Uganda. Wastewater secondary effluent was obtained from Urbana & Champaign Sanitary District in Illinois, US.

Human serum from human male AB plasma (USA origin, sterile-filtered) was purchased from Sigma-Aldrich.

In-Vitro Selection of the HAdV-Specific Aptamer

A schematic diagram of the in vitro selection process is shown in FIG. 1A.

First round of in vitro selection: The heat denatured ssDNA library (1 nmol) was mixed with 50 ul of $6\times10^5$ pfu/ml infectious virus in a total volume of 350 ul of SELEX buffer (20 mM TRIS, 100 mM NaCl and 2.5 mM $MgCl_2$, pH 7.2) and incubated for 2 h at room temperature. Then, the unbound sequences were removed using an Amicon Ultra-0.5 100 kD filter, followed by 4 times washed with 400 μl of SELEX buffer to ensure to remove all the unbound sequences. To elute the bound sequences, the filter with the virus and bound sequences was heated for 15 min at 95° C. in the presence of 8 M urea and centrifuge, collecting the fraction that flow through the filter in a new tube. Then, to concentrate and desalt the DNA, an Amicon Ultra-0.5 10 kD filter was used with washing 2 times with SELEX buffer (300 μl each time). Then, 1 μl of the eluted ssDNA was used to quantify the amount of DNA by qPCR, and the remaining pool was used as a template for amplification of bound sequences by PCR (30 cycles of 1 min at 95° C., 30 s at 52° C., 1 min at 72° C., followed by 10 min at 72° C.) to obtain the dsDNA pool. The PCR was carried out in a total volume of 50 μl with the reverse primer labelled with a biotin, using a GoTaq Flexi DNA Polymerase (Promega). Finally, ssDNA was recovered by streptavidin-coated magnetic beads. 1 μl of the recovered ssDNA was used to quantify the amount of DNA by qPCR and the remaining DNA was used for the following round.

$2^{nd}$ to $11^{th}$ round of in vitro selection: Enriched pools (200 pmol) were heat denatured as described above, and mixed with 25 μl of $1\times10^5$ pfu/ml noninfectious virus in a total volume of 100 μl of SELEX buffer. After incubation for 1 h at room temperature, the unbound sequences were recovered using an Amicon Ultra-0.5 100 kD cutoff and washing 2 times with 100 μl of SELEX buffer. The unbound sequences that flowed through the filter were collected and incubated with 50 μl of $6\times10^5$ pfu/ml infectious virus in a total volume of 350 μl. From here the protocol is the same as for round 1.

All Amicon Ultra-0.5 filters were treated with 1 mM of T20 for 30 min to avoid unspecific adsorption of the library and pool sequences on the filter.

A new PCR reaction using unlabeled primers was performed to prepare the pools for next generation sequencing.

In-Vitro Selection Process Monitoring qPCR was used to monitor the SELEX process in two ways: testing the enrichment of the pools (elution yield) using an absolute quantification, and assessing sequence diversity of the pools (convergence of the aptamer species) by the melting curve (Luo et al., *Analyst* 142:3136-3139, 2017).

Real-time PCR conditions experiments were conducted in CFX Real-Time PCR System (BioRad) according to the manufacturer's instructions. All reactions were performed in 10 μl reaction volumes in 96-well plates for PCR. A standard qPCR mixture contained 5 μl SsFast EvaGreen Supermix (BioRad), 0.3 μl of 500 nM of each unlabeled primer, 3.4 μl of $H_2O$ and 1 μl DNA template. Thermal cycling consisted of an initial denaturation at 98° C. for 2 min followed by 40 cycles of denaturation at 98° C. for 5 s and annealing and extension at 52° C. for 10 s. After these amplification cycles, the melting curves analysis was performed from 65° C. to 95° C. Threshold cycle (Ct) values were determined by automated threshold analysis.

Deep Sequencing

Selected selection cycles (round 4, 6, 7, 8, 9, 10 and 11) were prepared for next-generation sequencing (NGS) analysis on Illumina HiSeq4000 platform, using Celero DNA Seq kit (Nugen). Briefly, end repair of fragmented DNA was performed, followed by adaptor ligation and PCR amplification to produce the final libraries. This kit incorporated different indexes that allow the sample analysis of 7 different rounds on one lane. After purification of the PCR product with Agencourt® AMPure XP Beads (Beckman Coulter), quantification of the DNA was carried out using a fluorescence method (Qubit kit—Broad Range), and equal amounts of each library containing specific indexes were mixed. After a quality control (concentration and fragment analyses of the DNA), 100 bp single end sequencing was carried out.

After demultiplexing, NGS data was analyzed using the FASTAptamer software (Alam et al., *Mol. Ther. Nucleic Acids* 4:e230, 2015). FASTAptamer-Count allows counting the number of times each sequence is sampled from a population and then ranking and sorting the sequences by abundance, while FASTAptamer-Enrich was used to calculate fold-enrichment for each sequence present in more than one round of the selection by dividing the RPM of the sequence from one population by the RPM in another.

Binding Affinity Tests

Enzyme-linked oligonucleotide assay (ELONA): ELONA was used to determine the binding affinity of the aptamer toward HAdV. Infectious HAdV ($6\times10^5$ pfu/ml) was coated on a microplate at room temperature for 2 h. After blocking with 100 μl of 5% bovine serum albumin (BSA) in phosphate-buffered saline for 1 h at room temperature, the biotin-labeled aptamer was added to the individual wells at various concentrations (0.1 to 100 nM) in the SELEX binding buffer and incubated for 1 h at room temperature. Horseradish peroxidase-conjugated streptavidin (1:500) was added and incubated for 45 min Color development was achieved by adding tetramethylbenzidine chromogen substrate (TMB). After adding 2 M $H_2SO_4$ as stop solution, the optical density at 450 nm ($OD_{450}$) was determined using a microplate reader. The same procedure was done for the free chlorine inactivated HAdV.

Thermofluorimetric Analysis (FA): Thermofluorimetric analysis (TFA) measures the fluorescence of a mixture of DNA and intercalating dye as a function of temperature (Damase et al., *ACS Comb. Sci.* 20:45-54, 2018; Hu et al., *Anal. Methods* 7:7358-7362, 2015). Intercalating dyes are only highly fluorescent when bound to double-stranded DNA. At high temperatures, double-stranded regions of the DNA melts and the fluorescence decreases. TFA monitors aptamer melting, leveraging the changes in thermodynamic stability afforded by target binding.

Binding of Apt-HAdV aptamer to HAdV was tested with melting curve analysis. A solution containing 20 nM of aptamer was annealing at 95° C. and cooled slowly at room temperature. Then, a mixture of 2 μl of the aptamer solution, 2 μl of SYBR Gold (1:100 dilution), and 15 μl of HAdV solution at different concentrations was added to individual wells. All sets of samples were placed in the qPCR and melting curve data was acquired, by triplicates, between 20° C. and 95° C., at 0.5° C. per min with data collection at 30 s intervals.

A control experiment was carried out in the same conditions but without Apt-HAdV aptamer for study the background contribution of HAdV. Also, a negative control was performed by changing the Apt-HAdV aptamer for a non-specific DNA, containing the same length but a random sequence, to confirm that the detected changes corresponded to the specific interaction between Apt-HAdV aptamer and the infectious HAdV. Finally, a selectivity test was performed repeating the assay with the Apt-HAdV aptamer sequence and other virus commonly present in water samples, Coxsackie virus.

Nanopore Fabrication

12 μm polyethylene terephthalate (PET) foils were exposed at the UNILAC heavy in accelerator of the GSI Helmholtz Centre for Heavy Ion Research to single GeV heavy ions. Each highly energetic ion creates along its trajectory through the polymer foil a highly localized damage trail known as ion-track. The ion-track has a diameter of a few nm and can be selectively removed by chemical hydrolysis, e.g., etching. Chemical etching was performed in an in-house built electrochemical cell, where the irradiated foil is inserted between two-compartments. The compartments were filled with 6 M NaOH, and 6 M NaOH+0.05% (in volume) Dowfax 2a1, respectively. Etching was continued for 6 minutes at 60° C., to fabricate bullet-like shaped nanochannels, e.g., a combination of longer cylindrical and shorter parabolic segments. Single nanochannels with bullet-like shape exhibit non-linear current voltage characteristics due to the asymmetric shape of the reduced size tip and the negative charges stemming from the carboxylate groups generated on the polymer surface during the hydrolysis. Average dimensions of the as-obtained bullet-like shaped nanochannels were: (a) tip=55±5 nm, (b) base: 900±100 nm, as described previously (Perez-Mitta et al., *Nano Lett.* 18:3303-3310, 2018).

Modification of Nanopore—Immobilization of the Aptamer

After etching, the single nanochannel membranes were modified with the HAdV aptamer by EDC/Sulfo-NHS coupling between the carboxylate groups in the nanopore and an amino modified Apt-HAdV aptamer. On the one hand the amino modification at the 5' end with the longer linker available in IDT (12 $CH_2$-groups) was chosen to avoid nanopore surface from interfering with the aptamer binding to its target ($NH_2$—$C_{12}$-Aptamer, Table 1). On the other hand, incorporating the amine modification at the 3' end was chosen to compare the effect of the different orientation of the HAdV aptamer on the surface. In this case with a shorter linker (6 $CH_2$-groups) available in IDT (3AmMO-Aptamer, Table 1).

The PET single nanochannel membrane was incubated first with 20 mM EDC and 30 mM Sulfo-NHS in buffer 100 mM MES pH 5.5 for 45 min at room temperature, to form the sulfo-NHS esters. In the second step, after washing with the same buffer, the membrane was incubated overnight with a solution of 2 μM amino-DNA in buffer 100 mM MES pH 5.5 at room temperature.

Current-Voltage Measurements

Current-voltage (I-V) curves were recorded using a potentiostat (CHI620, CH Instruments) in a four-electrodes set up (working, working sense, reference and counter-electrode). In this way, conductance variations arising from changes in the nanochannel can be monitored and separated from other processes in solution or on electrode surfaces. Both the working and counter-electrode were platinum wires while the reference and working-sense were commercial silver/silver chloride (Ag/AgCl/3 M KCl) electrodes. In all experiments working and counter electrodes were placed at the base and tip of the channels, respectively. A 0.1 M KCl solution was used as electrolyte.

Measurement of the Virus Samples 1.5 ml of the sample containing the virus was incorporated in the compartment facing the larger base of the aptamer-modified nanochannel, while a SELEX buffer was filled in the compartment facing the channel tip. After 30 minutes incubation, the compartments were rinsed with distilled filtered water and the 0.1M KCl electrolyte was inserted in both compartments to record the I-V characteristics between 1 and −1 V at 100 mV/s (3 cycles).

Rectification Efficiency

In all experiments the definition for the rectification efficiency ($f_{rec}$) is given by, $$f_{rec} = \pm\left|\frac{I(1\text{ V or }-1\text{ V})}{I(-1\text{ V or }1\text{ V})}\right|$$

where the current I in the numerator corresponds to the largest current value in the high conductance state, whereas the current in the denominator is the lowest current value corresponding to the low conductance state. Additionally, if the higher current corresponds to a negative voltage, the rectification factor is multiplied with −1. This definition simplifies the notation. In order to compare results stemming from different nanopores, a normalized rectification efficiency ($f_{rec}$norm) is defined by dividing each $f_{rec}$ from a specific nanochannel by $f_{rec}$ value in presence of just buffer ($f_{rec,0}$), $$f_{rec}norm = \frac{f_{rec}}{f_{rec,0}}$$

In the case of human serum samples, the $f_{rec}$norm is calculated by dividing each $f_{rec}$ from a specific nanochannel by $f_{rec}$ value of that nanochannel in presence of human serum ($f_{rec,0}$).

Example 2

Development of DNA Aptamers Selective for Infectious Hadv

Human Adenovirus (HAdV) was selected to demonstrate the possibility of selecting aptamers that can differentiate infectious from noninfectious virus without the need to disrupting the virus to extract nucleic acid for detection as commonly used by other methods. HAdV has a high stability and long-term viability in the environment, and is a leading cause of potentially acute infections of the respiratory and digestive tracks especially in children worldwide. Respiratory illness is transmitted through poor hygiene, and gastroenteritis results from ingesting inadequately disinfected drinking water and contaminated recreational water.

To assess the infectivity of HAdV, a major challenge is finding a sensing molecule that can bind and recognize intact infectious HAdV, but not noninfectious HAdV or other viruses. To meet the challenge, DNA aptamers—DNA molecules that can recognize targets that often rival antibodies and yet are less expensive and more stable than antibodies—were chosen. Since DNA aptamers can be obtained using systematic evolution of ligands by exponential enrichment (SELEX) in a test tube (Elligton et al., *Nature* 346:818-822, 1990; Tuerk et al., *Science* 249:505-510, 1990), the SELEX was carefully designed to include both positive selection steps toward infectious HAdVs, (e.g., retain the DNA molecules that bind to infectious HAdVs), and counter selection steps for the same HAdVs that have been rendered noninfectious by $f_{rec}$ chlorine treatment, by discarding the DNA sequences that can bind to noninfectious HAdV. A schematic representation of the selection process is shown in FIG. 1A, and details of the positive and counter selections are given in Table 1 Example 1.

The SELEX was performed using the whole virus as the target, instead of a biomarker for the virus. In doing so, the goal was to select aptamers that will bind to the targets in its native state, without the need for disruption of the virus (Sefah et al., *Nat. Protoc.* 5:1169-1185, 2010; Kacherovsky et al., *Nat. Biomed. Eng.* 3:783-795, 2019). To prepare the infectious HAdV (serotype 2) was propagated using human lung A549 carcinoma cells. The noninfectious HAdV was prepared by $f_{rec}$ chlorination, the most common disinfection technique worldwide, using a protocol reported previously (Page et al., *Water Res.* 43:2916-2926, 2009; Gall et al., *Environ. Sci. Technol.* 49:4584-4590, 2015). After allowing for a free chlorine exposure of 2.33 $mgCl_2$×min/L, which was high enough to ensure complete inactivation of HAdV, the sample was quenched and filtered to remove reagents. The noninfectious HAdV was then resuspended in the same buffer as that used for the infectious HAdV sample. Since this method does not depend on known biomarkers, it can be readily applied to new emerging viruses that appear worldwide with increasing rate of occurrence.

Figures 2A, 2B:
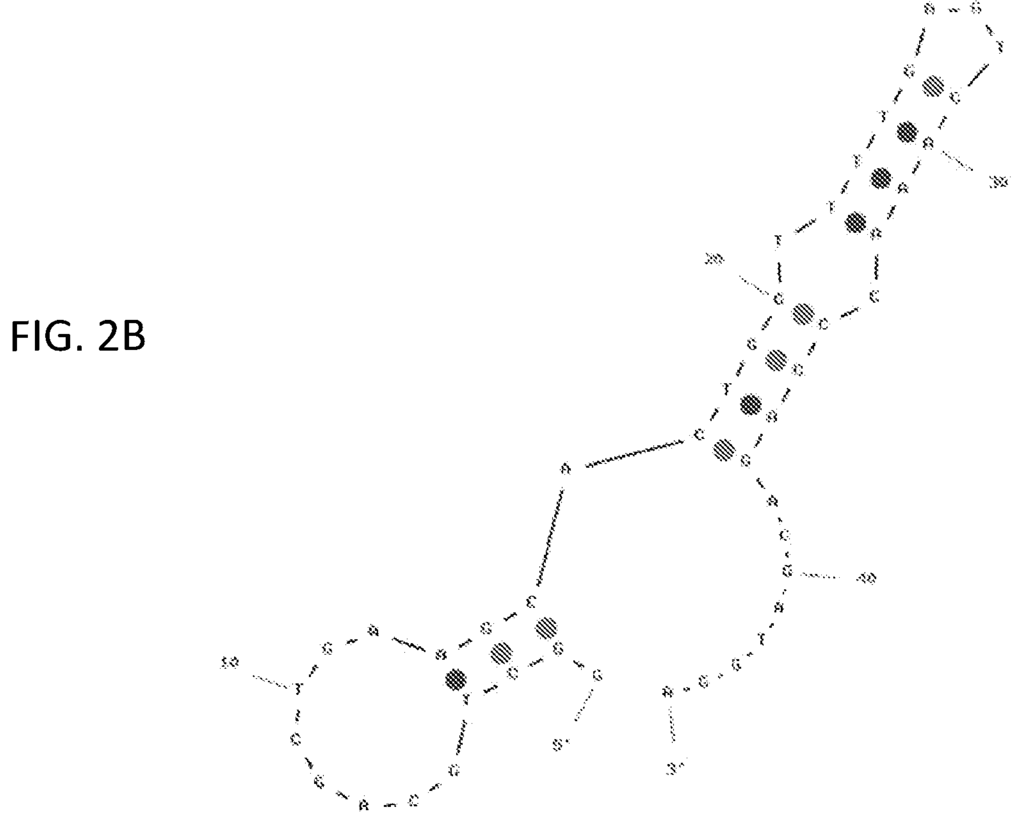
FIGS. 2A and 2B show reads per millions (RPM) obtained by the analysis of the NGS data for Ap-HAdV sequence as a function of the selection rounds, using FASTAptamer-Count (FIG. 2A) and the predicted more stable secondary structure of the aptamer based on Mfold software (SEQ ID NO: 5.

To monitor the selection progress, qPCR technique was used. The elution yield, defined by the ssDNA bound to infectious HAdV over the added ssDNA, initially increased with each early rounds of SELEX and leveled out at around Round 7, suggesting an enrichment of the pools (FIG. 1B). By comparing the melting curves after qPCR to assess sequence diversity of the DNA pools (Luo et al., *Analyst* 142:3136-3139, 2017) a convergence of the DNA pool from mostly random sequences with low melting temperatures to more conserved sequences with higher melting temperature was observed (FIG. 1C). To determine which sequences were responsible for the binding of the virus target, next-generation sequencing (NGS) was used for Rounds 4, 6, 7, 8, 9, 10 and 11 of the SELEX, allowing tracking the evolution of individual sequences over multiple selections rounds, and to identify "winner" aptamer sequences that were enriched with subsequent rounds. From this analysis, a sequence, named Apt-HAdV, that has been enriched over consecutive selection rounds was identified (FIG. 2A). This Apt-HAdV is predicted by Mfold software to display a highly structured secondary structure that contains two stem loop regions that may be responsible for recognizing the virus (FIG. 2B).

To characterize the binding affinity of the Apt-HAdV to the virus target, two different techniques were used. First, an enzyme-linked oligonucleotide assay (ELONA) was used to obtain the dissociation constant ($K_d$) to the virus. FIG. 1D shows the OD450 as a function of the Apt-HAdV aptamer concentration for a fixed concentration of virus. For binding to the infectious HAdV, a $K_d$ of (0.9±0.1) nM was obtained after fitting the data; this $K_a$ is at least one order of magnitude stronger than previous reported $K_d$s of aptamers for other viral particles. When the same assay was repeated with noninfectious HAdV, no binding was observed under the same conditions. These results indicate that the Apt-HAdV aptamer displays high selectivity toward the infectious over noninfectious HAdV.

Figures 3A, 3B, 3C:
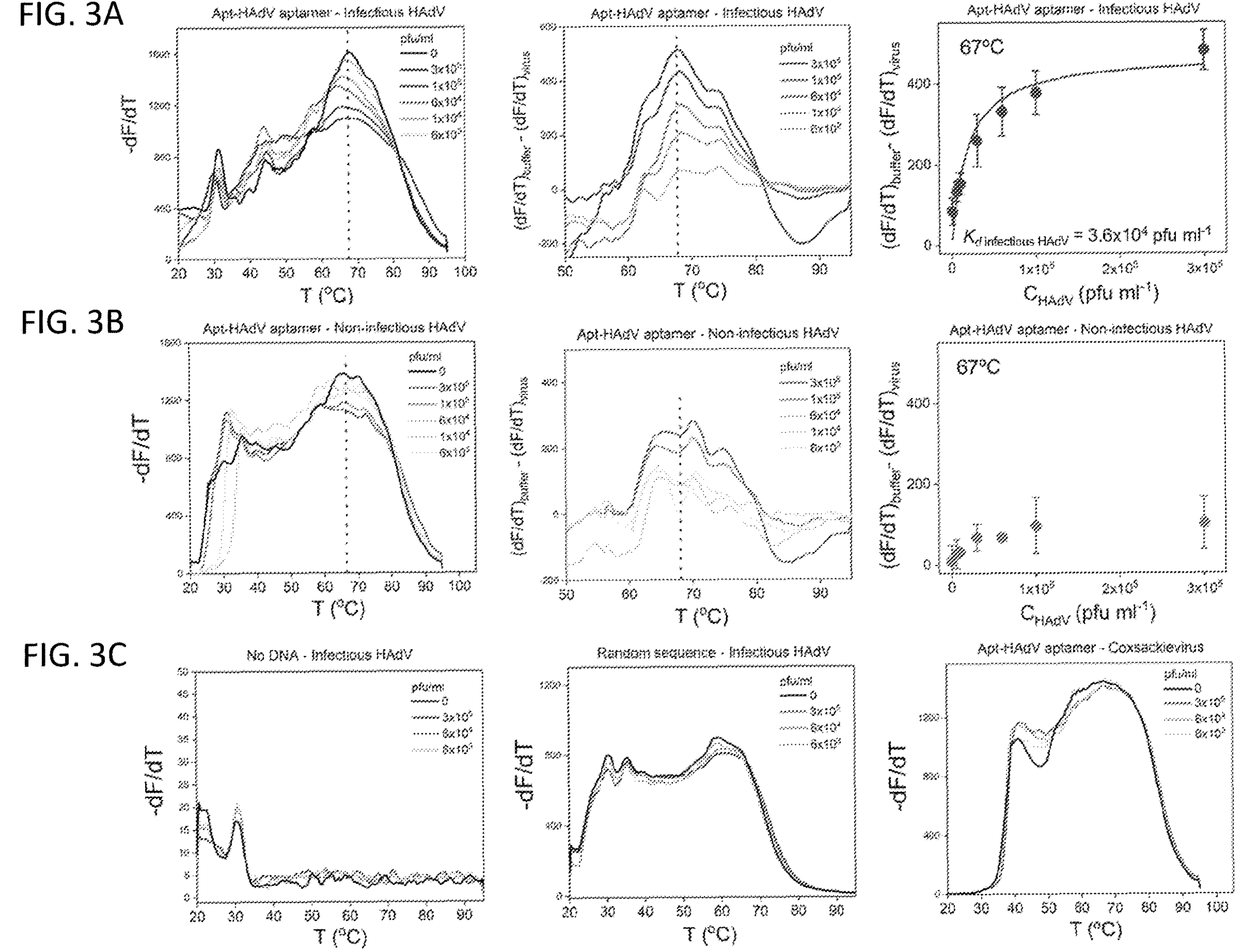
FIGS. 3A-3C are thermofluorimetric analysis (TFA) of binding interaction of Apt-HAdV aptamer and HAdV using qPCR.

To corroborate the finding from ELONA, thermofluorimetric analysis (TFA) was used to monitor how Apt-HAdV's binding to its target affects its conformational transitions as the temperature increases leveraging the changes in thermodynamic stability afforded by the binding. A relative decrease in the transition at 67° C. (−dF/dT maximum) was observed with increasing concentration of the infectious HAdV, from which a $K_d$ of $(3.6±0.6)\times10^4$ pfu/ml was obtained (FIG. 3A). When the same assay was repeated with noninfectious HAdV, a minimal change in the 67° C. −dF/dT was observed (FIG. 3B), confirming excellent selectivity of the Apt-HAdV aptamer toward the infectious HAdV. The above results strongly suggest that the Apt-HAdV aptamer has a remarkable high affinity and selectivity for the infectious HAdV over noninfectious HAdV.

Example 3

Development of Solid State Nanopore Sensor with Integrated Apt-HAdV

Having demonstrated high selectivity of Apt-HAdV toward infectious HAdV, the next step was converting the aptamer into a sensor with high sensitivity, preferably down to a single virus within volume sampled. To achieve the goal, the Apt-HAdV was integrated into a solid-state nanopore, which has been recently established as a portable sensing platform for many targets with high sensitivity, due to the remarkable signal amplification capacity that have been demonstrated. In this respect, solid-state nanopores derivatized with recognition sites can be considered as nanofluidic elements whose ion transport properties may be precisely modulated in the presence of specific biological signals, thus leading a simple and reliable signal amplification mechanism.

Figure 5:
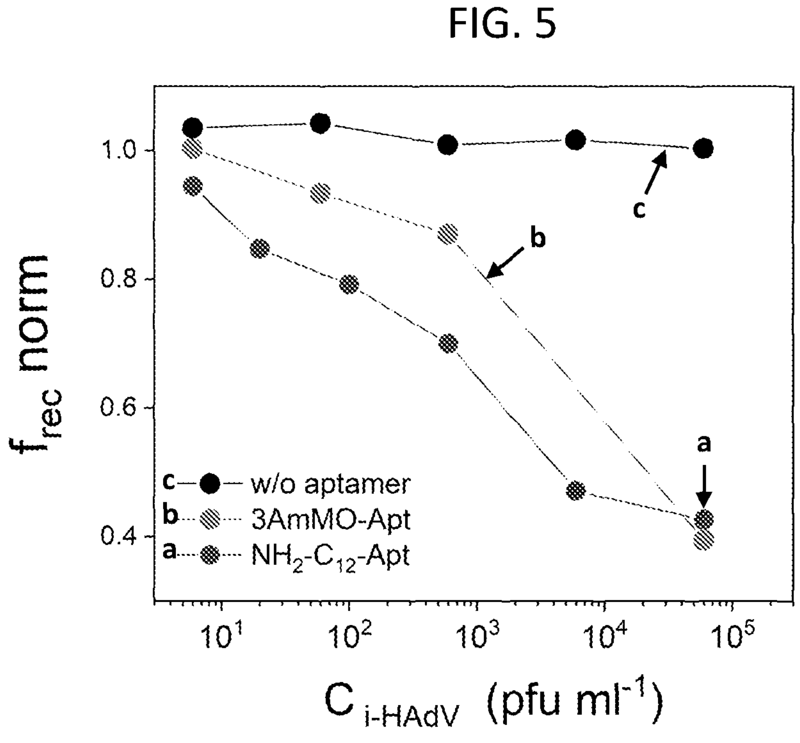
FIG. 5 shows normalized rectification efficiencies versus logarithm of the infectious HAdV concentration obtained for different amino modifications of the HAdV aptamer. To prevent nanopore surface from interfering with the aptamer binding to its target, a spacer was added between the amine group and the aptamer. Also, the effect of different orientation of the HAdV aptamer on the surface was studied by introducing the amino modification on different ends of the sequence. Nanopore without aptamer, nanopore modified with 3AmMO-aptamer (3' modification), and nanopore modified with $NH_2$-$C_{12}$-aptamer (5' modification).
Figure 6:
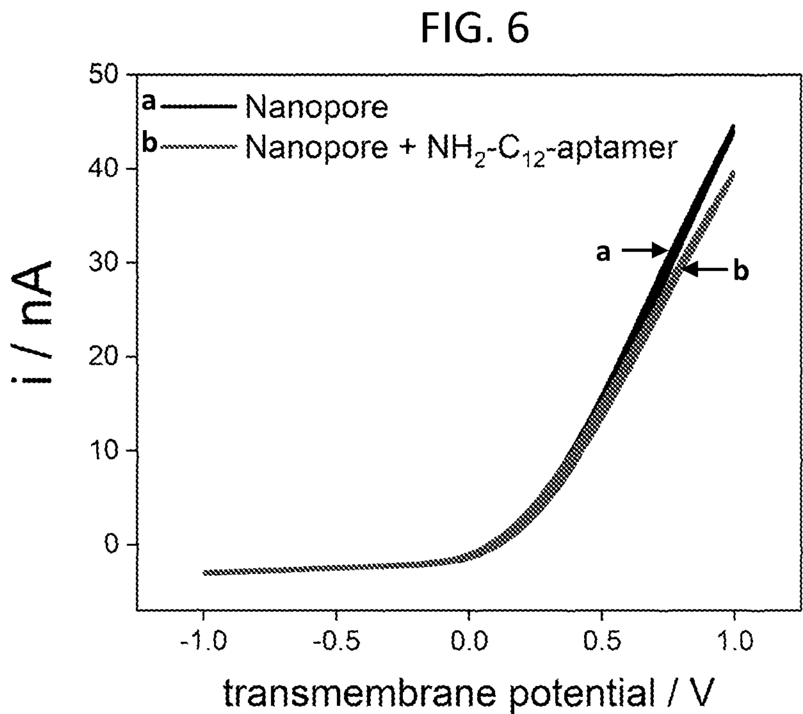
FIG. 6 shows I-V curves of a nanopore system before and after the modification with $NH_2$-$C_{12}$-aptamer.

In order to construct a highly sensitive sensor, single nanochannel membranes made of polyethylene terephthalate (PET) were fabricated by single swift heavy ion irradiation, followed by a chemical etching process to control the shape and size of the nanopore, as reported previously (Perez-Mitta et al., *Nano Lett.* 18:3303-3310, 2018). Then, the Apt-HAdV aptamer was immobilized onto the inner wall of the nanopore by EDC/Sulfo-NHS coupling between the carboxylate groups present on the surface of the nanopore after the etching and the $NH_2$-modified Apt-HAdV aptamer (FIG. 4A). To decrease nanopore surface from interfering with the aptamer binding to its target, a spacer was added between the amine group and the aptamer (FIG. 5). The above modification procedure was verified by the current-voltage (I-V) measurements, showing a decrease in the current after grafting the aptamer onto the nanopore (FIG. 6), due to a reduction of the nanochannel cross section by the presence of the DNA.

Figure 7:
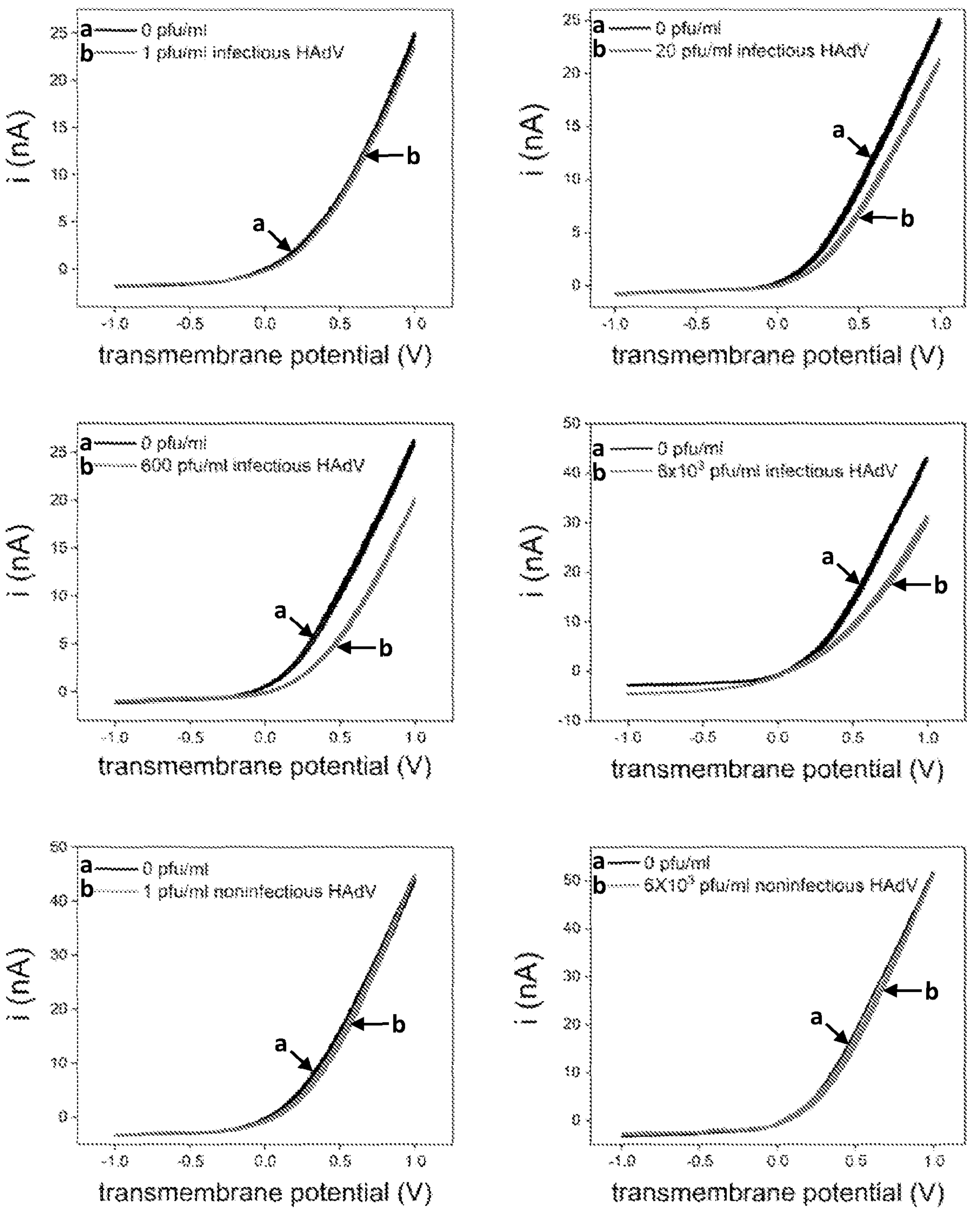
FIG. 7 shows I-V curves for different nanopores modified with $NH_2$—$C_{12}$-aptamer, without virus (0 pfu/ml) and with different concentrations of infectious HAdV or noninfectious HAdV. Comparing the differences in the I-V curves without virus and with virus for the same membrane, it can be seen that even for a high concentration ($6\times10^3$ pfu/ml) of noninfectious HAdV no changes were observed, while for 1 pfu/ml of infectious virus there is a decrease in the current at 1V.
Figure 9:
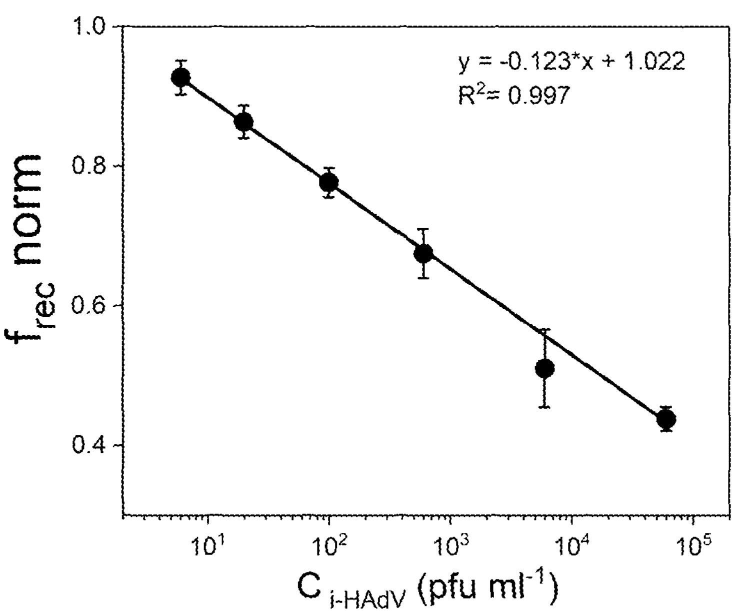
FIG. 9 is a graph showing linear dependence of normalized rectification efficiencies versus logarithm of infectious HAdV concentration with linear fitting. Each data point represents the mean and standard deviation of 3 replicates.
Figure 10:
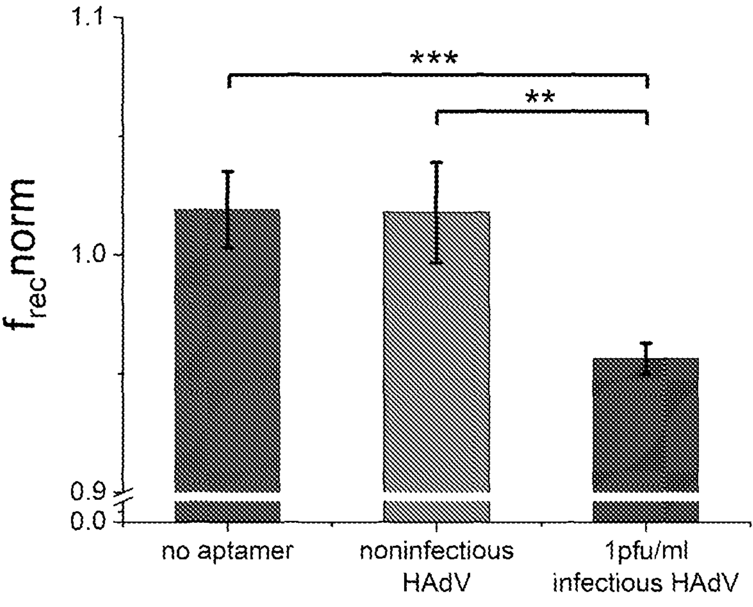
FIG. 10 illustrates that the aptamer-nanopore system can detect 1 pfu/ml of infectious HAdV. Normalized rectification efficiency of 1 pfu/mL of infectious HAdV after aptamer immobilization on the nanopore. The mean and SD of $f_{rec}$norm for the different concentrations of infectious HAdV showed in FIG. 4B when no aptamer is grafted in the nanopore, and the mean and SD of $f_{rec}$norm for the different concentrations of noninfectious HAdV showed in FIG. 4B after immobilization of the aptamer in the nanopore are shown. Two-tailed Student's t test; p<0.01, *p<0.001, bars represent mean±SD.
Figure 15:
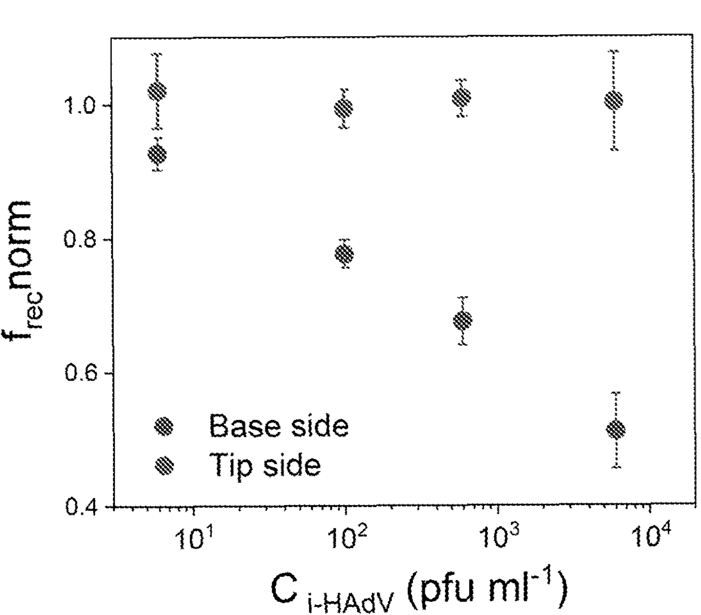
FIG. 15 shows normalized rectification factor versus logarithm of the infectious HAdV concentration after 30 min incubation of the virus solution facing the base side of the nanopore and facing the tip side. No changes in the $f_{rec}$norm were observed when the virus sample was applied to the reservoir facing the narrow side (tip) of the nanopore. This indicates that the virus needs to be able to enter the nanopore to bind to the aptamer coating the inner surface of the nanopores. Due to the reduced tip size, this is possible only from the base. Tip diameter <50 nm, base diameter: ≈900 nm.

The sensitivity of the aptamer-nanopore system for detection of HAdV was first assessed by evaluating the ion transport properties changes as a function of the HAdV concentrations (FIG. 7). The virus samples were applied to the reservoir facing the base of the nanopore to allow the virus to enter the nanopore and bind to the aptamer that is coated on the inside of the pore (scheme in FIG. 8A; FIG. 15). It appears that the capture of the virus inside the nanopore produces a strong confinement, as the nanopore is ten times larger than the virus, resulting in a consequent signal amplification. The rectification efficiencies ($f_{rec}$) were normalized by dividing each $f_{rec}$ from the samples containing viruses by the $f_{rec}$ of the same system in presence of just buffer ($f_{rec}0$), in order to account for slight differences in the I-V curves characteristics after nanopores etched. FIG. 4B shows the normalized rectification efficiency ($f_{rec}$norm) versus the concentration of virus. First, no significant change in the $f_{rec}$norm was observed when the aptamer was not incorporated in the nanopore (FIG. 4B). Once the aptamer was grafted in the inner wall of the nanopore, the $f_{rec}$norm decreased with increasing amount of the infectious HAdV (FIG. 4B), due to a change in the effective pore size with the virus incorporation, and thus in the ion transport properties. From the curve, the infectious HAdV was quantified in a broad range, from 6 to $6\times10^4$ pfu/ml (FIG. 9), with the ability to detect the HAdV down to 1 pfu/mL (FIG. 10). At such a low level of detection, the diffusion of the viral particles into the nanopore can be rate limiting.

Based on the linear regression obtained (FIG. 9), it is possible to define the limit of detection as LoD=3*σ/m, and the quantification limit as LoQ=10*σ/m, where m is the slope of the linear calibration (m=0.123) and 6 is the standard deviation of the intercept (σ=0.0076). Then, to obtain the LoD and LoQ in pfu/mL units, the antilogarithm is calculated, because the linear regression is obtained from a logarithm scale in the x axis. Thus, the LoD=1.5 pfu/mL and LoQ=4 pfu/mL.

In addition, using a two-tailed Student's t test, the mean of the $f_{rec}$norm signal obtained for 1 pfu/mL of infectious HAdV was compared with a) the mean $f_{rec}$norm value for different concentrations of infectious HAdV when no aptamer is grafted in the nanopore, and b) the mean $f_{rec}$norm for different concentrations of noninfectious HAdV after immobilization of the aptamer in the nanopore. In both cases, these values were significantly different to the $f_{rec}$norm for 1 pfu/mL of infectious HAdV, with at least 99.9% and 99% confidence, respectively (FIG. 9). Thus, 1 pfu/mL of HAdV is indeed producing a signal distinguishable from these blanks.

Figure 16A:
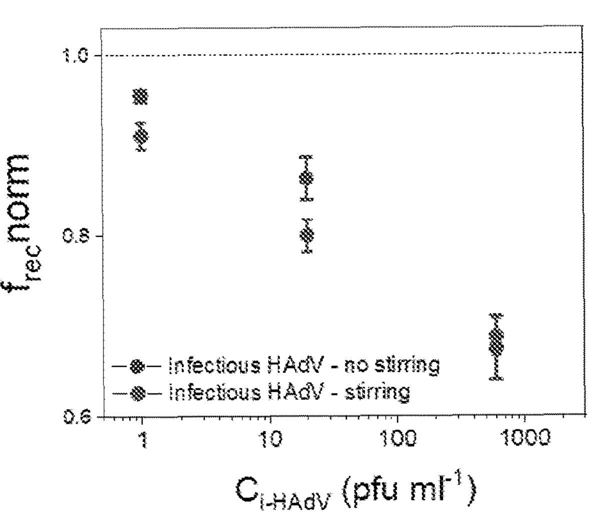
FIGS. 16A and 16B show the effect of stirring on $f_{rec}$norm.
Figure 16B:
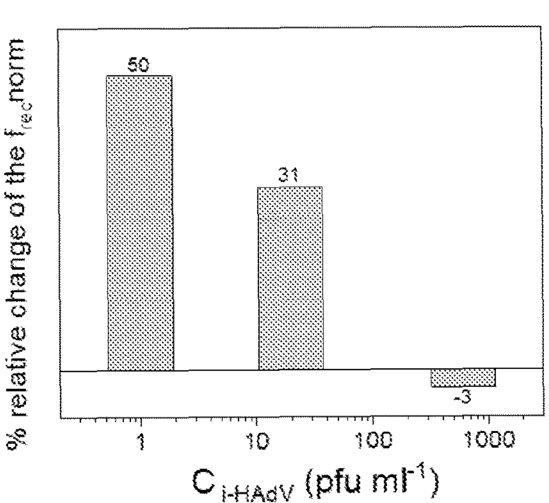

To determine the contribution of mass transport on the nanopore signal experiments, magnetic stirring was incorporated during the virus incubation step (FIGS. 16A and 16B). Transport of virus to the nanopores was limiting the nanopore signal only for concentrations lower than 20 pfu/mL. However, incubation for thirty minutes was sufficient to obtain enough signal for detection, due to the high sensitivity of the nanopore.

To test the selectivity of the aptamer-nanopore sensor, the rectification current was measured in the presence of noninfectious HAdV. No significant change in the $f_{rec}$norm was observed in the presence of a wide range of concentrations, indicating that the selectivity of the nanopore system is governed by the aptamer. Moreover, the aptamer-nanopore system showed a remarkable selectivity against ultraviolet light-inactivated HAdV-2 (UV-inact), Coxsackievirus B5 (CoxV), and Murine Norovirus (MNV) even at high concentrations of these viruses (FIG. 4C), demonstrating viral infectivity status-selectivity as well as species-specificity of the Apt-HAdV aptamer. Furthermore, the aptamer-nanopore system was tested with different infectious HAdV serotypes, such as HAdV-2, HAdV-5 and HAdV-40. As shown in FIG. 4D, Apt-HAdV aptamer recognized different types of infectious adenovirus, including HAdV-40, a type of HAdV that cannot replicate well in cell culture system and thus is not as readily detectable by the standard plaque assay.

Figure 11:
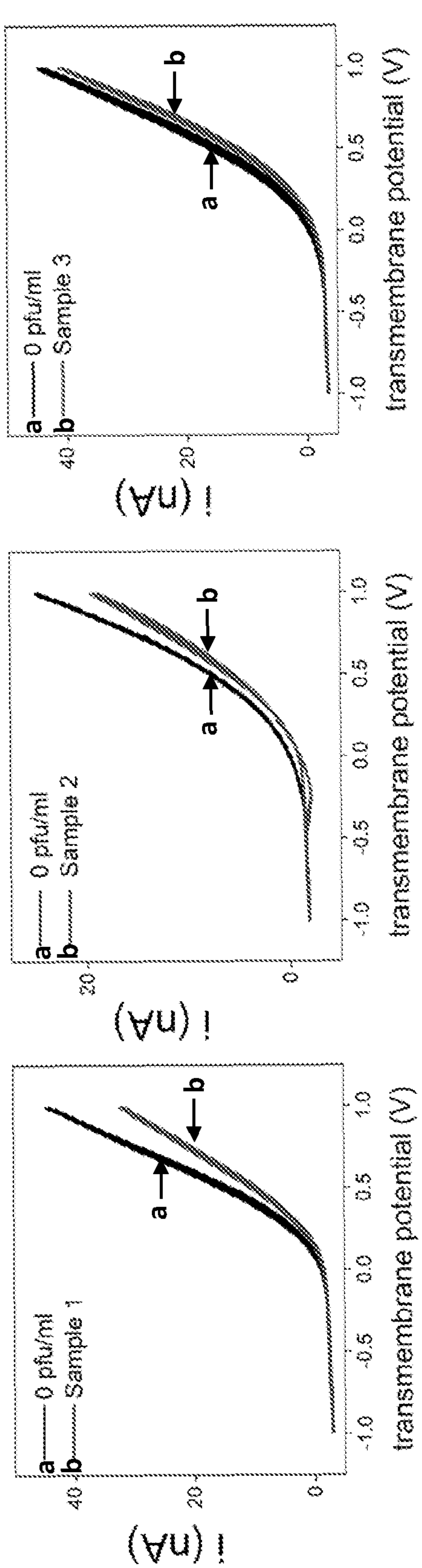
FIG. 11 shows I-V curves for three samples prepared by treating an infectious HAdV sample ($7.2\times10^3$ pfu/ml) with free chlorine and taking aliquots at different timepoints to obtain different degree of inactivation but the same total amount of virus: 90% (sample 1), 99% (sample 2), and 99.9% (sample 3). The differences in the f indicate that the aptamer-nanopore sensor can detect different infectious HAdV concentrations even when the total amount of virus is the same within different samples.

To determine if the sensor has the capability of quantify infectious HAdV in a sample in which a portion of the HAdV has been inactivated, an infectious HAdV sample was treated with $f_{rec}$ chlorine and quenched the disinfection at different timepoints to obtain samples with different percentages of HAdVs that have been inactivated (90%, 99% and 99.9%). The $f_{rec}$norm was found to increase when the percentage of inactivation increased, even if the total concentration of HAdV remained the same, demonstrating the ability of the aptamer-nanopore system to quantify infectious HAdV in a mixture of infectious and non-infectious HAdV (FIG. 11), even when the latter are present at 1 to 3 orders of magnitude higher concentration. These results were benchmarked with the culture method—plaque assay, and no significant difference was observed between the two methods (FIG. 8B).

Figure 12A:
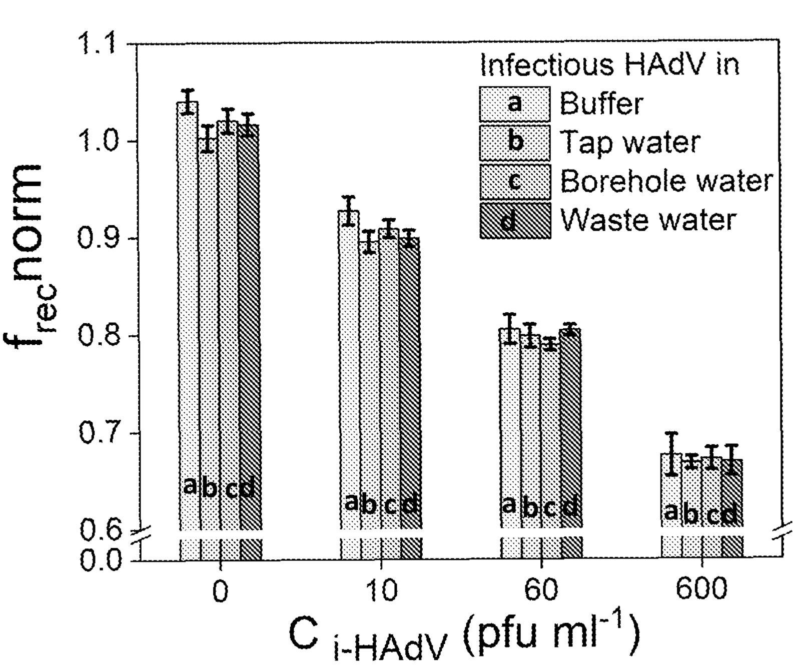
FIG. 12A is a graph showing normalized rectification efficiency obtained for different concentration of infectious HAdV that were spiked in drinking water and wastewater. The $f_{rec}$norm measured for the same concentration of infectious virus in buffer was included for comparison. n=3 technical replicates (mean±SD).
Figure 12B:
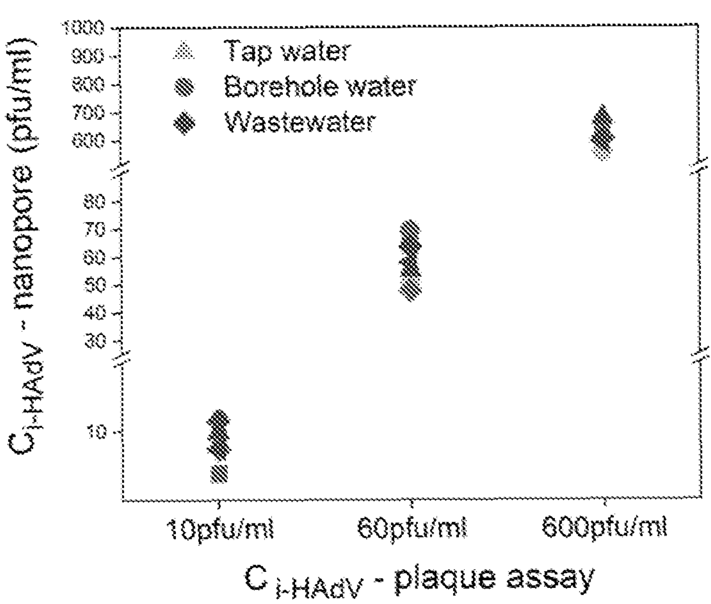
FIG. 12B shows individual values for each concentration (triplicate) for different environmental water samples.
Figure 13:
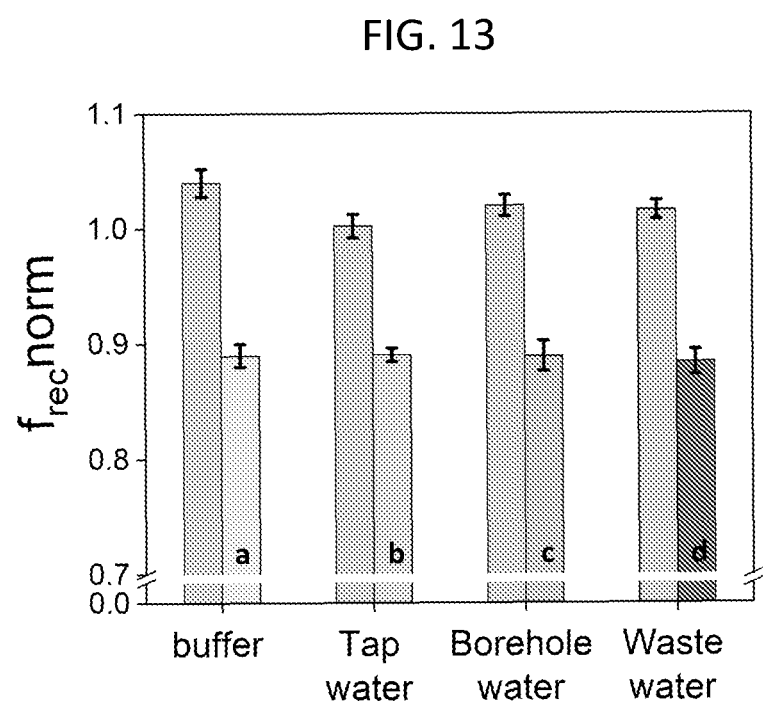
Figures 14A, 14B, 14C, 14D:
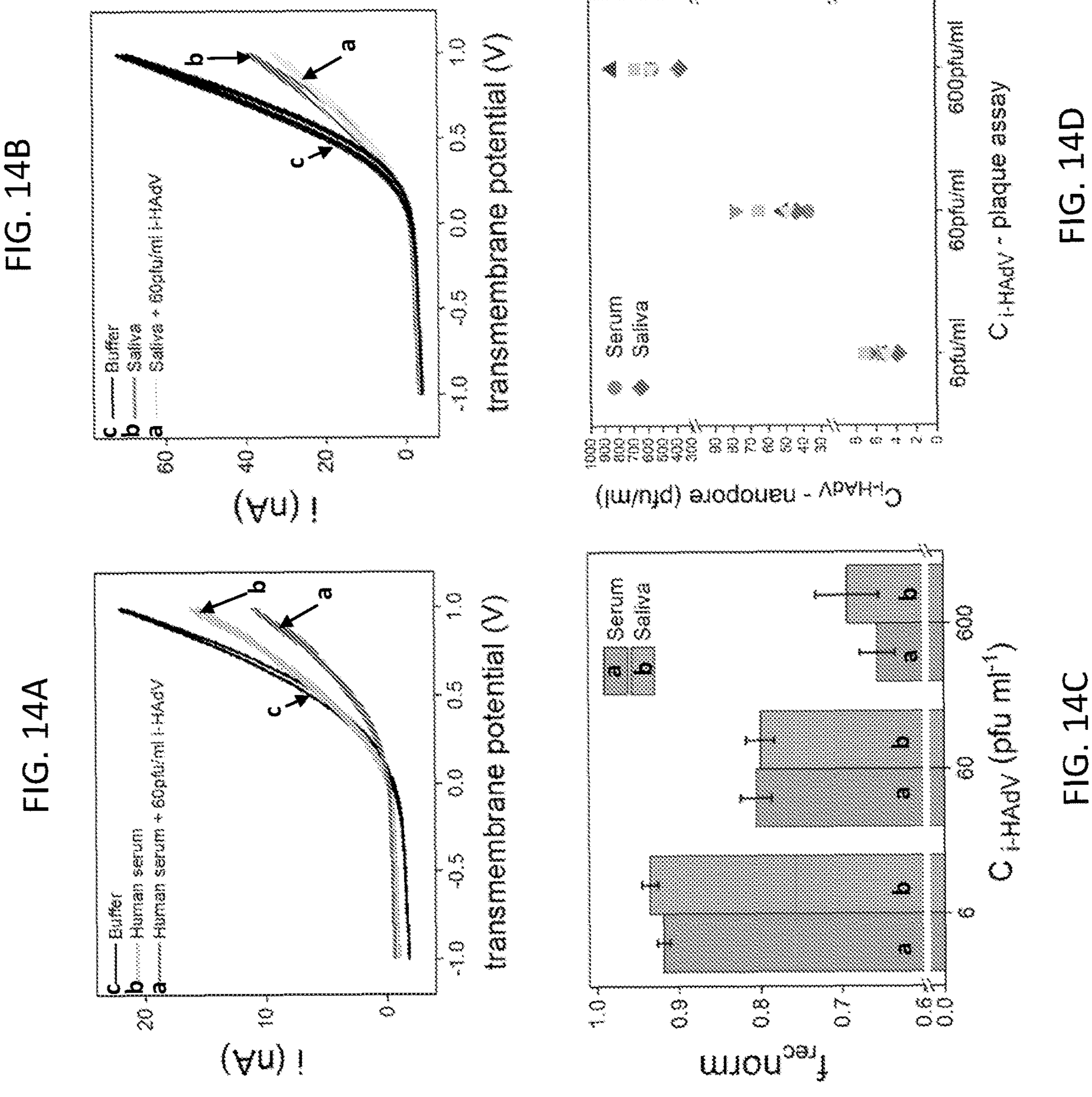
FIGS. 14A-14D show testing of human samples.

Furthermore, to test the ability of the aptamer-nanopore system to quantify infectious HAdV in real environmental samples, a drinking water sample from a tap in Champaign (IL, US), a more complex drinking water sample from a borehole in a secondary school in Uganda (Africa), and a wastewater effluent sample (IL, US) were tested. Since no HAdV were detected initially in these samples by qPCR methods, the samples were spiked with different concentrations of infectious HAdV. The three samples were measured using the aptamer-nanopore system without any pretreatment of the water (FIGS. 12A and 12B) and the results were compared with the plaque assay results (FIG. 8C). For both drinking water samples, the recovery yield was (102.5±5.5) %, while for the wastewater effluent the recovery yield was (95±7)%, indicating that the sensor can quantify infectious HAdV in real water samples despite the presence of potential interfering background substances. Furthermore, when a 99.9% inactivated HAdV was spiked into these environmental waters, it was possible to quantify 10 pfu/ml of infectious HAdV in the presence of $7\times10^3$ pfu/ml total HAdV, in all cases (FIG. 13). Overall, these results demonstrate that the performance of the aptamer-nanopore system is largely unaffected by the complex matrices of the samples.

Figures 8A, 8B, 8C, 8D:
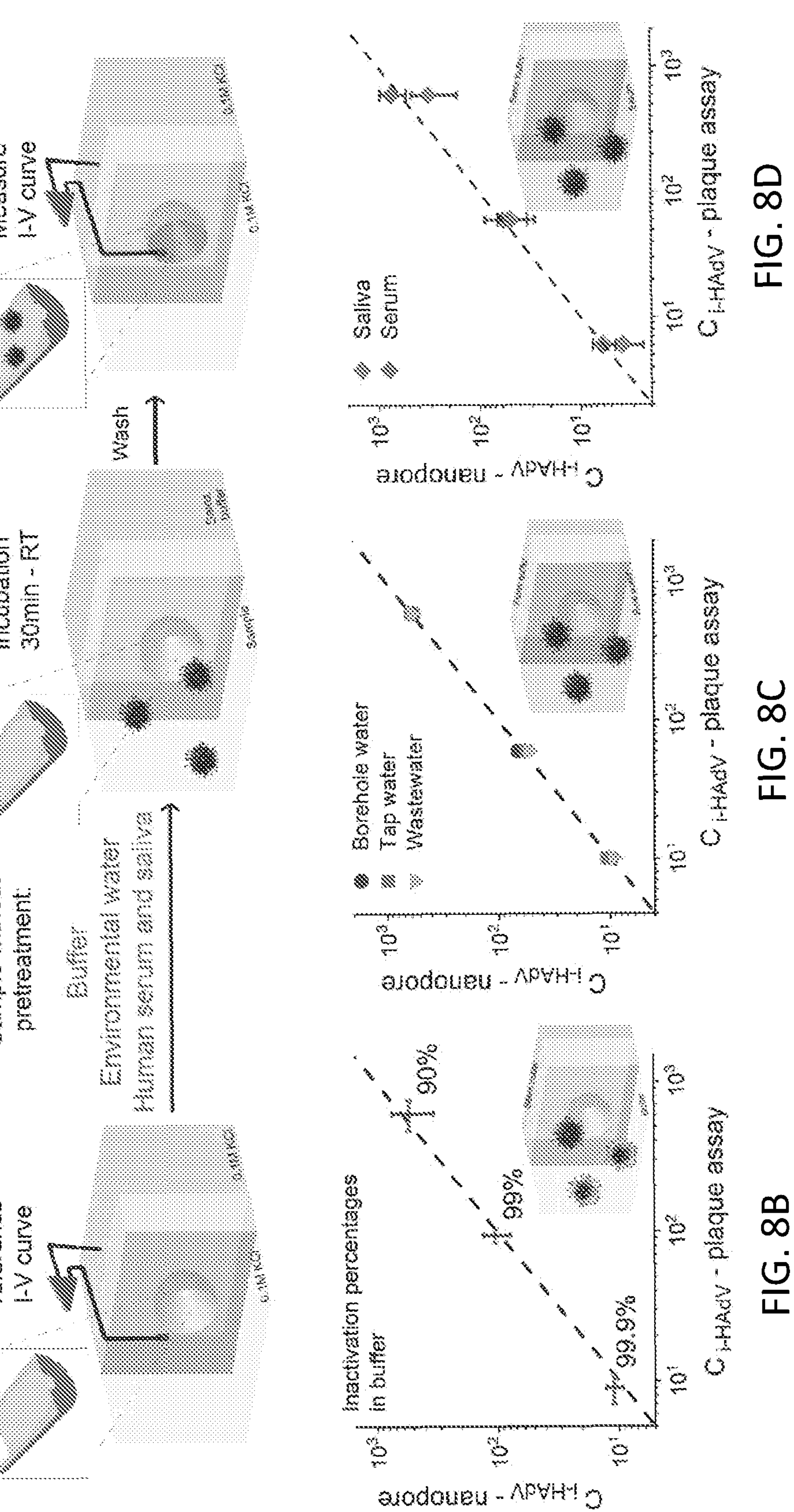
FIGS. 8A-8D show direct quantification of infectious HAdV on real samples with aptamer-nanopore system.

Finally, to explore the possibility of extending this aptamer-nanopore assay for rapid diagnostics of infectious HAdV directly from bodily fluids, human serum was spiked with infectious HAdV and a decrease in the $f_{rec}$norm was observed with different concentrations of infectious HAdV (FIGS. 14A-14D), and their performance was similar to those measured in a buffer (FIG. 8D).

Example 4

Comparative Study of Detection Methods

Infectious HAdV concentration was quantified using plaque assays and benchmarked results with the HAdV aptamer methods with this, as it is still considered the gold standard method to quantify infectious virus, since methods such as qPCR and immunoassays are not capable of distinguishing noninfectious/inactivated virus from active virus. It is likely that the efficiency of infectivity determined by plaque assay is lower than 100% because some infective viruses that reach the surface of host cells in the plaque assay might not locate protein receptors involved in the initial attachment steps of the infection cycle, ultimately resulting in the formation of plaques.

Although to date there is no method to determine what portion of the overall concentration of infective virions is obtained by plaque assay, a comparison could be made between results from plaque assays and qPCR measurements of genome copies in the same samples. In a previous study, HAdV-2 samples were quantified with both plaque assay and qPCR and revealed a ratio of ≈150 copies/pfu (Gall et al., *Environ. Sci. Technol. Lett.* 3:185-189, 2016). Unfortunately, the number of genome copies could not be considered to directly correspond to infective viruses because some copies could be associated with incompletely assembled virions not capable of infection. An important point revealed by the stirring test data in FIGS. 16A and 16B is that the regression has a stronger linear dependence compared to that of the tests without stirring. Extrapolation of the linear regression to $f_{rec}$norm=1 would result in an intercept of approximately 0.1 pfu/mL, suggesting that the sensor would have a sensitivity approximately one order of magnitude higher than that of the plaque assay. These results suggest that 1/15 genome copies could potentially correspond to infective viruses. Such a possibility is plausible because the aptamer method targets capsid proteins that are synthesized in the final steps of the infection cycle, and so the possibility that the signal corresponds to infective viruses is higher. If so, the concentration of infectious virions would be ten times that determined by plaque assay. This result indicates that, in the nanopore, a single infective particle in the sample is not necessarily detected, but the signal corresponds to an order of magnitude higher number, indicating that the same or higher detection limit as the gold standard method, plaque assay is reached, with a rapid and simple test. Moreover, this result highlights that plaque assays likely underestimate infectious virus concentration.

Example 5

Detection of SARS-CoV-2

Since the selection methods described herein do not depend on known biomarkers to differentiate infectious and non-infectious viruses, it can be readily applied to newly emerging viruses, which have been appearing worldwide at an increasing rate, without any information about the inactivation mechanism. To demonstrate the generality of the methods, the sensor was applied to detect SARS-CoV-2, the newly emerged coronavirus responsible for the COVID-19 pandemic. To retain the advantages of applying a whole-virus in vitro selection approach in applying the sensor to SARS-CoV-2, in vitro selection was performed using a pseudotyped SARS-CoV-2 virus. The pseudotyped virus is generated from a lentivirus (HIV) that displays the SARS-CoV-2 spike (S) protein within the viral envelope, and thus closely mimics the surface and entry mechanism of SARS-CoV-2 but is defective in continuous viral replication. Since the SELEX strategy to differentiate infectious from noninfectious viruses depends only on the surface of the viruses, this pseudotyped virus could be used.

Figure 17:
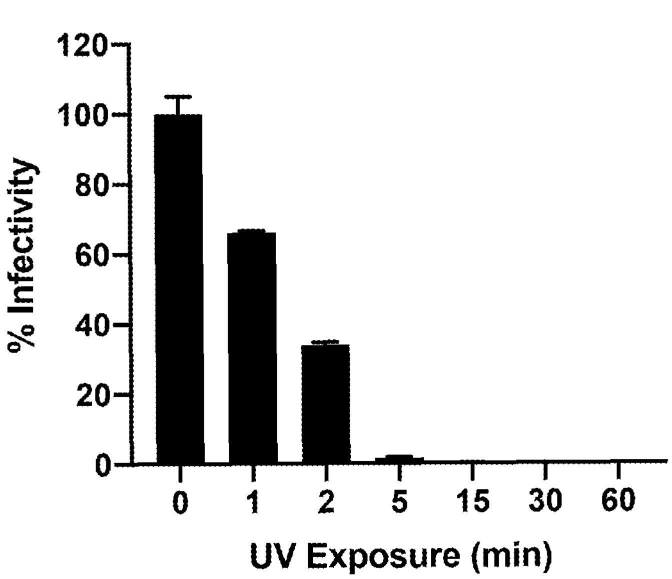
FIG. 17 illustrates monitoring the UV-light inactivation of SARS-CoV-2 pseudovirus at different exposure times by a luciferase assay. In the case of pseudotyped particles, it is not possible to perform a plaque assay.
Figure 18A:
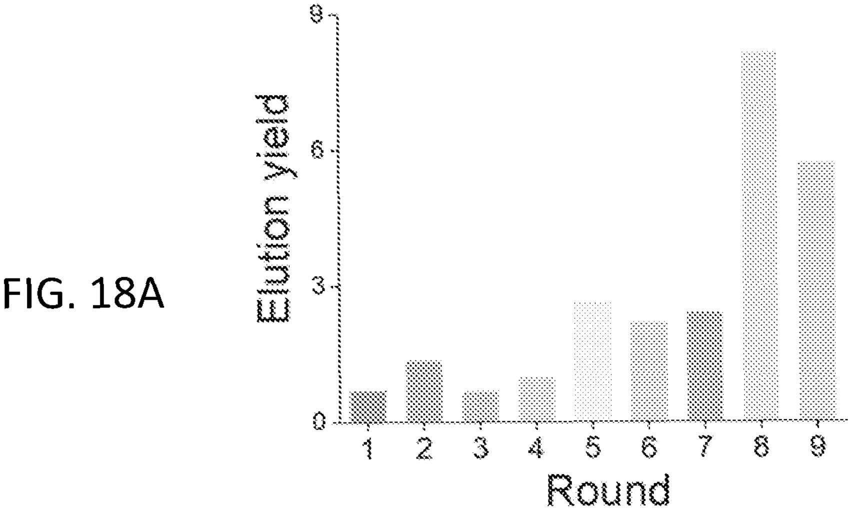
FIGS. 18A-18C show development of a SARS-CoV-2 aptamer.
Figures 18B, 18C, 19:
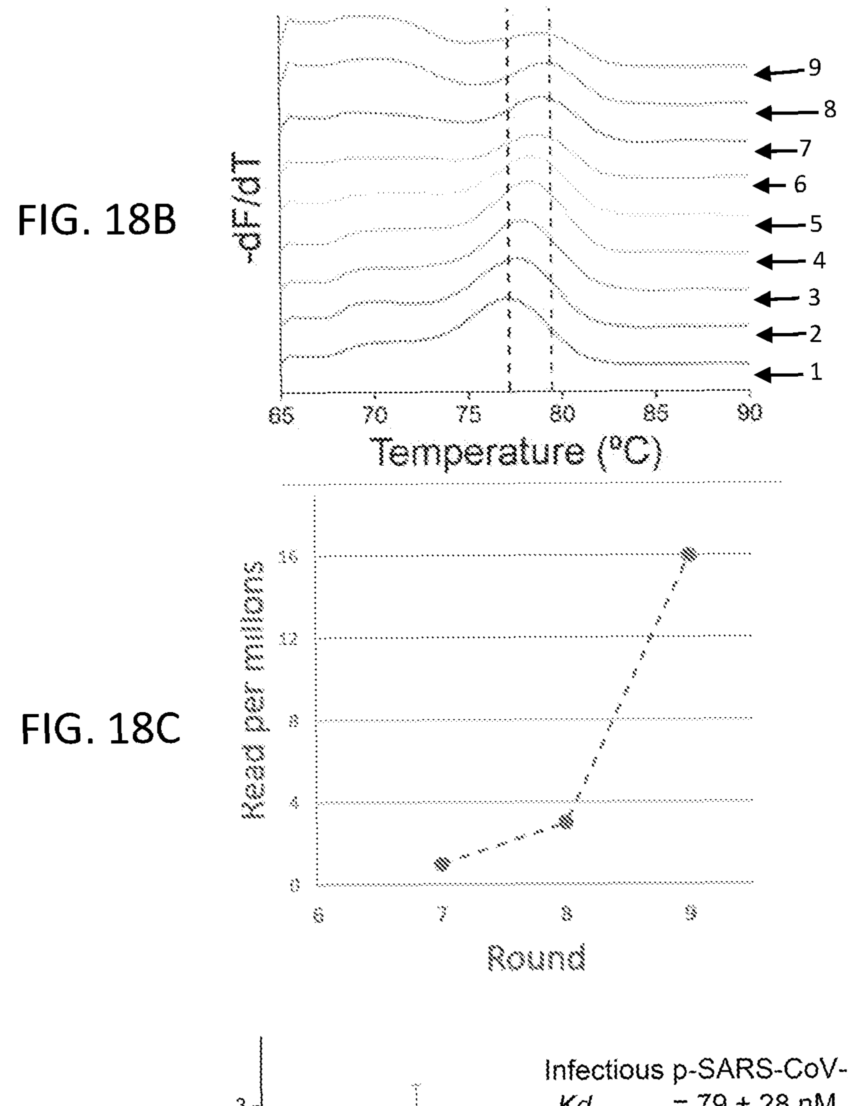
FIG. 19 is a graph of binding curves obtained from the ELONA assay after the immobilization of $5\times10^8$ copies/mL pseudotyped SARS-CoV-2 on a 96-well plate. The dissociation constant ($K_d$) of SARS2-AR10 sequence for the active pseudotyped SARS-CoV-2 was 79 nM, while no change in the absorbance at 450 nm was observed for the inactive pseudotyped SARS-CoV-2. n=3 technical replicates (mean±SD).\
Figures 20A, 20B, 20C:
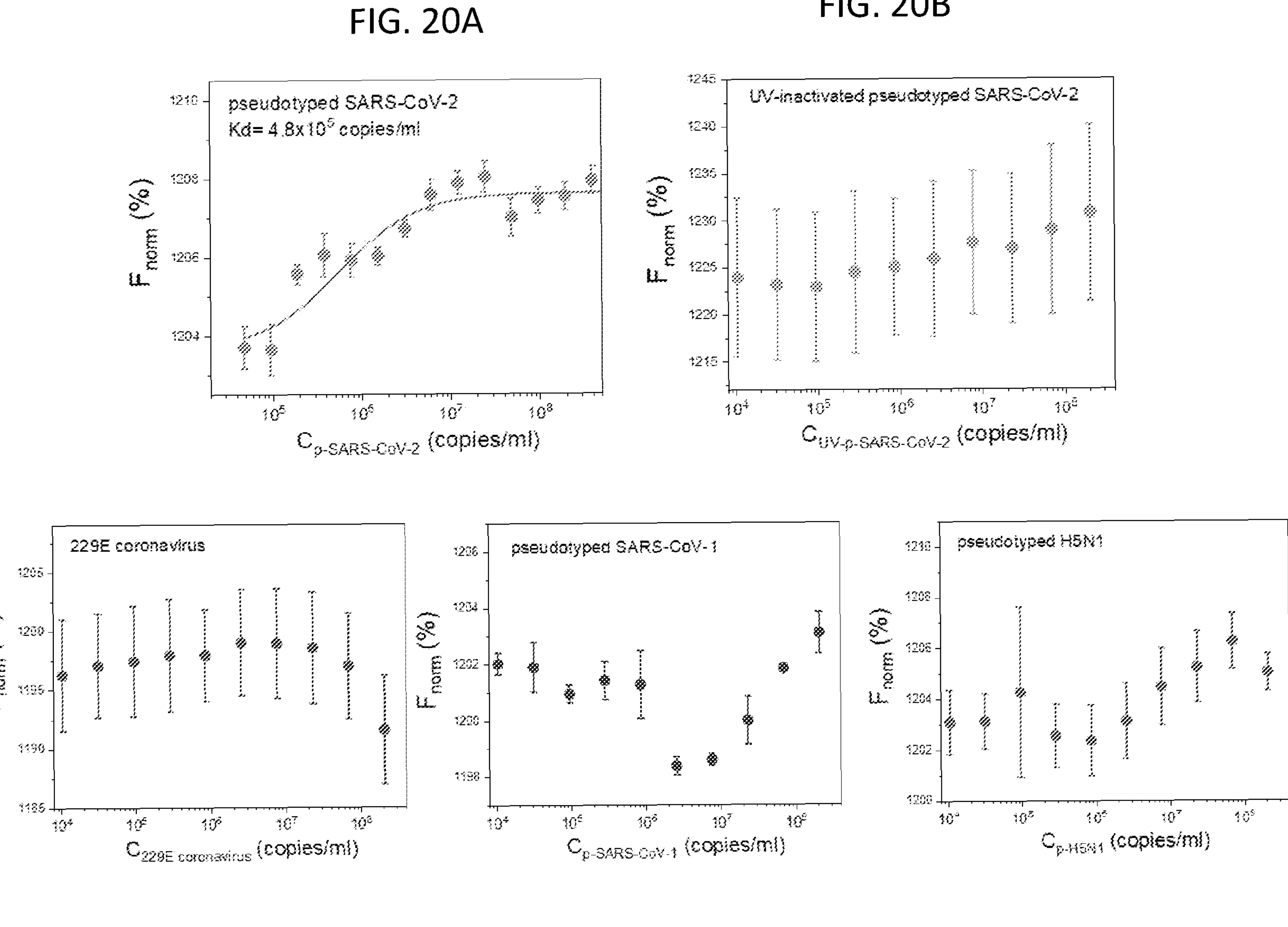
FIGS. 20A-20C show MST results for active pseudotyped SARS-CoV-2 (FIG. 20A), UV-inactivated pseudotyped SARS-CoV-2 (FIG. 20B) and other viruses, including 229E coronavirus, pseudotyped SARS-CoV-1, and pseudotyped H5N1 (FIG. 20C, left to right). SARS2-AR10 was labeled with FAM at the 5' end and its concentration was fixed at 250 nM. n=3 technical replicates (mean±SD).

To achieve high selectivity against active SARS-CoV-2 over inactive SARS-CoV-2, counter selection against UV-light inactivated pseudotyped SARS-CoV-2 was performed (FIG. 17). UV-inactivation produces damage in the genome and in the proteins on the surface of the virus, while largely maintaining the intact virus structure. Furthermore, to obtain an aptamer with the ability to distinguish against other viruses, counter-selection against a lentivirus pseudotyped with SARS-CoV-1 S protein and a lentivirus pseudotyped with influenza hemagglutinin 5 and neuraminidase 1 proteins (H5N1) was incorporated. Ten rounds of selection were performed (FIGS. 18A and 18B). After sequencing different rounds with HTS, a sequence, named SARS2-AR10 (Table 2), was identified that showed good enrichment over subsequent selection rounds (FIG. 18C). ELONA results showed a $K_d$ of 79±28 nM with high selectivity against UV-inactivated pseudotyped SARS-CoV-2 (FIG. 19), and Microscale Thermophoresis (MST) also showed that SARS2-AR10 bound to active SARS-CoV-2 but not to UV-inactivated pseudotyped SARS-CoV-2 or other viruses like 229E coronavirus, pseudotyped SARS-CoV-1, or pseudotyped influenza H5N1 (FIGS. 20A-20C), demonstrating the high selectivity of SARS2-AR10 toward active SARS-CoV-2.

TABLE 2

SARS-CoV-2 DNA sequences

| Name | DNA sequence (5' to 3') | SEQ ID NO: |
|---|---|---|
| DNA library SARS-CoV-2 | ACCGTCAGTTACAATGCT$(N)_{45}$ GGCTGGACTATCTGTGTA | 8 |
| Forward primer (FwP) SARS-CoV-2 | ACCGTCAGTTACAATGCT | 9 |
| Reverse primer (RevP) SARS-CoV-2 | /**5Biosg**/TACACAGATAGT CCAGCC | 10 |
| SARS2-AR10 | CCCGACCAGCCACCATCAGCAA CTCTTCCGCGTCCATCCCTGCTG | 11 |
| $NH_2$—$C_{12}$-SARS2-AR10 | /**AmMC12**/CCCGACCAGCCACCA TCAGCAACTCTTCCGCGTCCATC CCTGCTG | 12 |

Figure 21A:
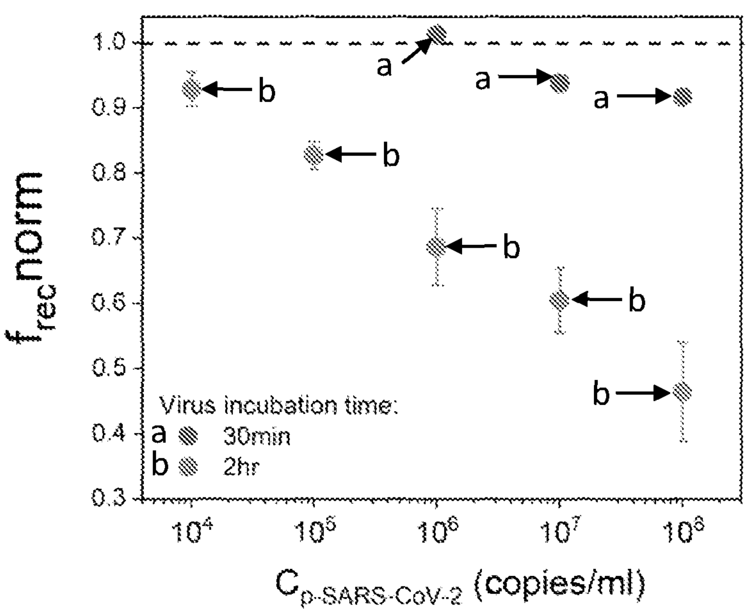
FIG. 21A shows normalized rectification factor versus logarithm of the active pseudotyped SARS-CoV-2 concentration after 30 min and 2 hr incubation time of the virus solution with the SARS2-AR10-nanopore system.
Figure 21B:
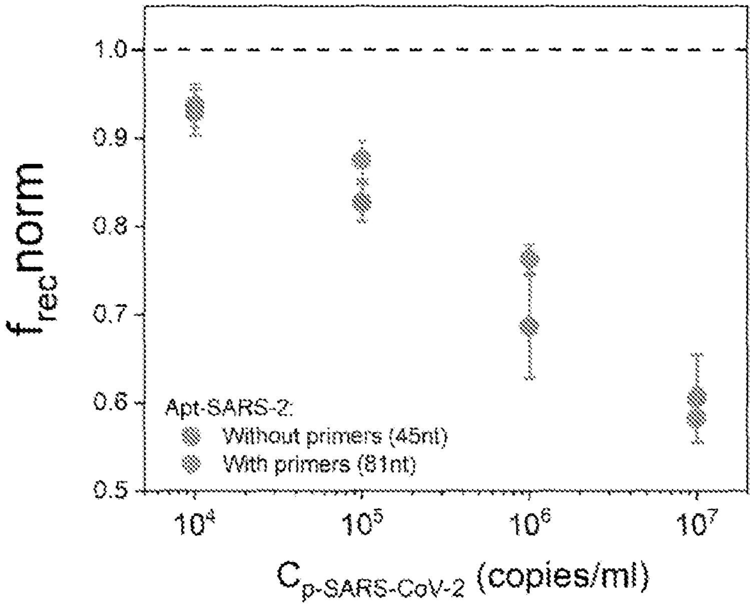
FIG. 21B is a comparison of the performance of the SARS2-AR10 with primers (81 nt) and without primers (45 nt).
Figure 22A:
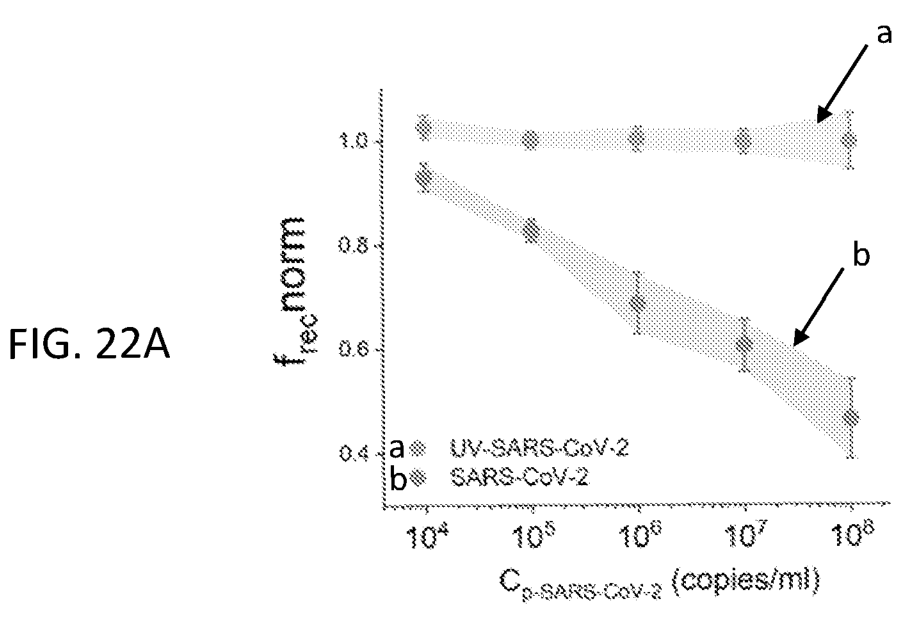
FIGS. 22A-22C show quantification of active pseudotyped SARS-CoV-2 with the aptamer-nanopore system.
Figure 22B:
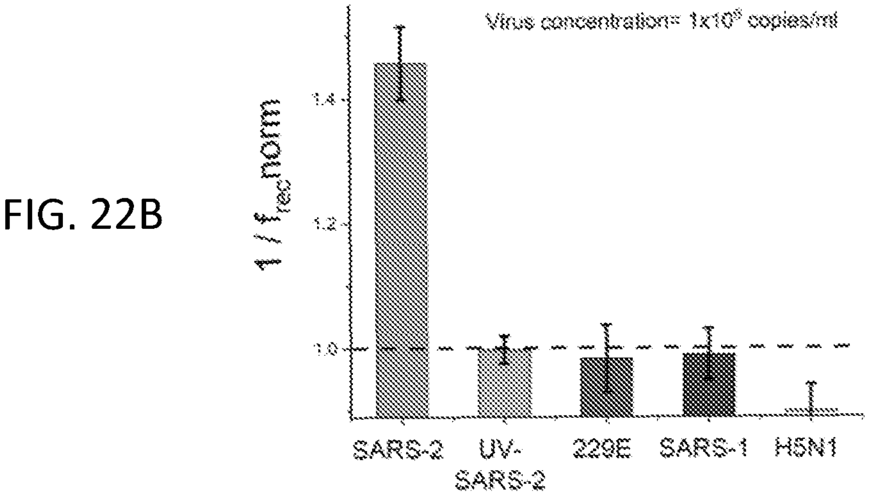

Modifications shown in bold type.
AmM = amino modification.
C12 = 12 carbon spacer.
5Biosg = biotin modification The SARS2-AR10-nanopore system to detect and quantify SARS-CoV-2 with different concentrations of active pseudotyped SARS-CoV-2 after 30 min and 2 hr virus incubation was determined (FIGS. 21A and 21B). An increase in the virus incubation time resulted in a higher sensitivity and lower detection limit. With 2 hr incubation, the sensor detected as low as $1\times10^4$ copies/mL and quantified a broad range of virus concentrations, from $1\times10^4$ copies/mL to $1\times10^8$ copies/mL (FIG. 22A). Thus the method can reach the lowest detectable concentrations in individuals that have tested positive for SARS-CoV-2 in saliva and nasal swabs. Furthermore, the lowest detectable concentration of the method ($1\times10^4$ copies/mL) is similar to the detection limit reached by RT-PCR ($3\times10^3$ copies/mL) and other nucleic acid detection methods, for instance those based on LAMP reaction ($5\times10^4$ copies/mL). The selectivity of our aptamer-nanopore sensor against inactive SARS-CoV-2 was further tested (FIG. 22A) and against an endemic coronavirus that produces the common cold, 229E coronavirus, as well as pseudotyped SARS-CoV-1 and H5N1 influenza virus (FIG. 22B). No significant change was seen, supporting the high selectivity of the sensor for active SARS-CoV-2 against inactive SARS-CoV-2, other coronaviruses, and influenza virus.

Figure 22C:
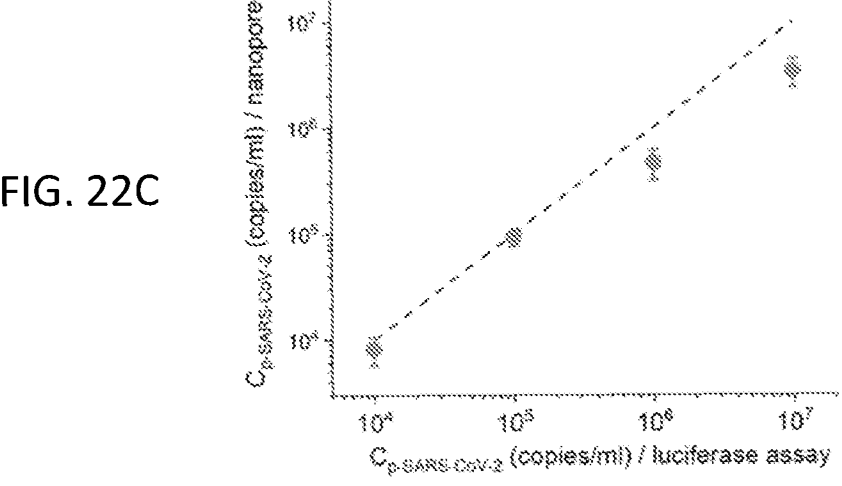
Figure 23:
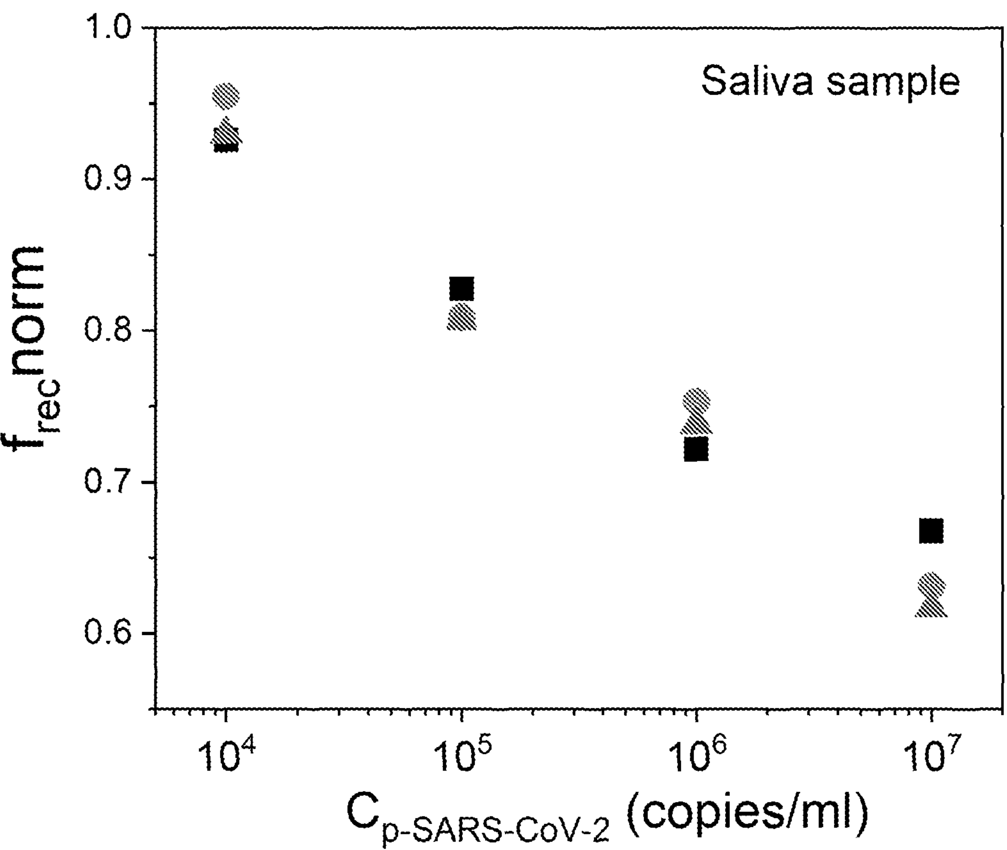
FIG. 23 shows normalized rectification factor versus logarithm of the active pseudotyped SARS-CoV-2 concentration spiked in human saliva sample. A total of 12 saliva samples were spiked with different concentrations of infectious pseudotyped SARS-CoV-2 and each sample was measured with a different nanopore membrane.

Finally, 12 human saliva samples were spiked with different concentrations of active pseudotyped SARS-CoV-2 and a decrease in the $f_{rec}$norm was observed with different concentrations of active SARS-CoV-2 (FIG. 23). The results showed a good correlation between the concentration calculated using the obtained $f_{rec}$norm in saliva compared with the concentration measured with luciferase assay (FIG. 22C), indicating that the aptamer-nanopore system can quantify pseudotyped SARS-CoV-2 in saliva without any pretreatment of the biological sample.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of detecting presence of a virus particle in a sample, comprising:

contacting the sample with a solid state nanopore comprising a plurality of virus-specific nucleic acid aptamers covalently linked to an inner wall of the solid state nanopore, wherein the solid state nanopore passes from a first surface to a second surface of a membrane and wherein the solid state nanopore comprises a diameter of about 50-60 nm at the first surface of the membrane and a diameter of about 800-1000 nm at the second surface of the membrane; and measuring a current-voltage curve in the solid state nanopore, wherein a decrease in current indicates presence of the virus particle in the sample.

2. The method of claim 1, wherein the membrane is present in a reservoir, wherein the reservoir is separated into two compartments by the membrane and the current-voltage curve is measured using two or more electrodes.

3. The method of claim 1, wherein the aptamer comprises a 3' or 5' amino modification.

4. The method of claim 3, wherein the aptamer comprises a spacer between the aptamer and the amino-terminal modification.

5. The method of claim 1, wherein the aptamer selectively binds an infectious, intact virus particle.

6. The method of claim 5, wherein the aptamer does not bind to a non-infectious, intact virus particle.

7. The method of claim 1, wherein the virus is a human adenovirus or a coronavirus.

8. The method of claim 7, wherein:

the human adenovirus is a human adenovirus type 2, a human adenovirus type 5, or a human adenovirus type 40; or the coronavirus is a SARS-COV-2 coronavirus.

9. The method of claim 8, wherein the aptamer comprises the nucleic acid sequence of SEQ ID NO: 5 or SEQ ID NO: 11.

10. The method of claim 1, wherein the method detects 10 pfu/ml or less of virus, 1 pfu/ml or less of virus, or wherein the method detects a single virus particle.

11. A solid state nanopore comprising a plurality of virus-specific aptamers covalently linked to an inner wall of the solid state nanopore, wherein the solid state nanopore passes from a first surface to a second surface of a membrane and wherein the solid state nanopore comprises a diameter of about 50-60 nm at the first surface of the membrane and a diameter of about 800-1000 nm at the second surface of the membrane.

12. The solid state nanopore of claim 11, wherein the aptamer comprises a 3' or 5' amino modification.

13. The solid state nanopore of claim 12, wherein the aptamer comprises a spacer between the aptamer and the amino-terminal modification.

14. The solid state nanopore of claim 11, wherein the aptamer selectively binds an infectious, intact virus particle.

15. The solid state nanopore of claim 14, wherein the aptamer does not bind to a non-infectious, intact virus particle.

16. The solid state nanopore of claim 11, wherein the virus is a human adenovirus or a coronavirus.

17. The solid state nanopore of claim 16, wherein:

the human adenovirus is a human adenovirus type 2, a human adenovirus type 5, or a human adenovirus type 40; or the coronavirus is a SARS-COV-2 coronavirus.

18. The solid state nanopore of claim 17, wherein the aptamer comprises the nucleic acid sequence of SEQ ID NO: 5 or SEQ ID NO: 11.

19. A membrane comprising a plurality of the solid state nanopores of claim 11.

20. A kit comprising the membrane of claim 19 and instructions for use.

21. A system comprising:

the membrane of claim 19; and one or more electrodes that are electrically coupled to the membrane.

* * * * *

SEQUENCE LISTING

```
<160> NUMBER OF SEQ ID NOS: 12

<210> SEQ ID NO 1
<211> LENGTH: 81
<212> TYPE: DNA
<213> ORGANISM: Artificial Sequence
<220> FEATURE:
<223> OTHER INFORMATION: HAdV DNA library
<220> FEATURE:
<221> NAME/KEY: misc_feature
<222> LOCATION: (19)..(63)
<223> OTHER INFORMATION: n is a, c, g, or t

<400> SEQUENCE: 1

gtccatcgtt cggtagtgnn nnnnnnnnnn nnnnnnnnnn nnnnnnnnnn nnnnnnnnnn     60

nnnggctaac tgtccacgat t                                                81


<210> SEQ ID NO 2
<211> LENGTH: 18
<212> TYPE: DNA
<213> ORGANISM: Artificial Sequence
<220> FEATURE:
<223> OTHER INFORMATION: HAdV forward primer

<400> SEQUENCE: 2

gtccatcgtt cggtagtg                                                    18


<210> SEQ ID NO 3
<211> LENGTH: 18
<212> TYPE: DNA
<213> ORGANISM: Artificial Sequence
<220> FEATURE:
<223> OTHER INFORMATION: HAdV reverse primer

<400> SEQUENCE: 3

aatcgtggac agttagcc                                                    18


<210> SEQ ID NO 4
<211> LENGTH: 20
<212> TYPE: DNA
<213> ORGANISM: Artificial Sequence
<220> FEATURE:
<223> OTHER INFORMATION: T20 oligonucleotide

<400> SEQUENCE: 4

tttttttttt tttttttttt                                                  20


<210> SEQ ID NO 5
<211> LENGTH: 45
<212> TYPE: DNA
<213> ORGANISM: Artificial Sequence
<220> FEATURE:
<223> OTHER INFORMATION: HAdV aptamer

<400> SEQUENCE: 5

ggctgcagct gaagcactgg ttttgagtca aacccagacg atgga                      45


<210> SEQ ID NO 6
<211> LENGTH: 45
<212> TYPE: DNA
<213> ORGANISM: Artificial Sequence
<220> FEATURE:
<223> OTHER INFORMATION: 3AmMO HAdV aptamer
<220> FEATURE:
<221> NAME/KEY: misc_feature
<222> LOCATION: (45)..(45)
<223> OTHER INFORMATION: 3' amino modification
```

<400> SEQUENCE: 6
ggctgcagct gaagcactgg ttttgagtca aacccagacg atgga 45

<210> SEQ ID NO 7
<211> LENGTH: 45
<212> TYPE: DNA
<213> ORGANISM: Artificial Sequence
<220> FEATURE:
<223> OTHER INFORMATION: NH2-C12-HAdV aptamer
<220> FEATURE:
<221> NAME/KEY: misc_feature
<222> LOCATION: (1)..(1)
<223> OTHER INFORMATION: 5' amino C12 spacer modification

<400> SEQUENCE: 7
ggctgcagct gaagcactgg ttttgagtca aacccagacg atgga 45

<210> SEQ ID NO 8
<211> LENGTH: 81
<212> TYPE: DNA
<213> ORGANISM: Artificial Sequence
<220> FEATURE:
<223> OTHER INFORMATION: SARS-CoV-2 DNA library
<220> FEATURE:
<221> NAME/KEY: misc_feature
<222> LOCATION: (19)..(63)
<223> OTHER INFORMATION: n is a, c, g, or t

<400> SEQUENCE: 8
accgtcagtt acaatgctnn nnnnnnnnnn nnnnnnnnnn nnnnnnnnnn nnnnnnnnnn 60
nnnggctgga ctatctgtgt a 81

<210> SEQ ID NO 9
<211> LENGTH: 18
<212> TYPE: DNA
<213> ORGANISM: Artificial Sequence
<220> FEATURE:
<223> OTHER INFORMATION: SARS-CoV-2 forward primer

<400> SEQUENCE: 9
accgtcagtt acaatgct 18

<210> SEQ ID NO 10
<211> LENGTH: 18
<212> TYPE: DNA
<213> ORGANISM: Artificial Sequence
<220> FEATURE:
<223> OTHER INFORMATION: SARS-CoV-2 reverse primer

<400> SEQUENCE: 10
tacacagata gtccagcc 18

<210> SEQ ID NO 11
<211> LENGTH: 45
<212> TYPE: DNA
<213> ORGANISM: Artificial Sequence
<220> FEATURE:
<223> OTHER INFORMATION: SARS-CoV-2 SARS2-A10 aptamer

<400> SEQUENCE: 11
cccgaccagc caccatcagc aactcttccg cgtccatccc tgctg 45

<210> SEQ ID NO 12
<211> LENGTH: 45
<212> TYPE: DNA

-continued

```
<213> ORGANISM: Artificial Sequence
<220> FEATURE:
<223> OTHER INFORMATION: NH2-C12-SARS2-A10 aptamer
<220> FEATURE:
<221> NAME/KEY: misc_feature
<222> LOCATION: (1)..(1)
<223> OTHER INFORMATION: 5' amino C12 spacer modification

<400> SEQUENCE: 12

cccgaccagc caccatcagc aactcttccg cgtccatccc tgctg                45
```